(12) United States Patent
Inoue et al.

(10) Patent No.: US 10,770,660 B2
(45) Date of Patent: Sep. 8, 2020

(54) HETEROCYCLIC COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Tomoka Hara, Kanagawa (JP); Yasushi Kitano, Kanagawa (JP); Hiromi Seo, Kanagawa (JP); Tatsuyoshi Takahashi, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 108 days.

(21) Appl. No.: 15/914,346

(22) Filed: Mar. 7, 2018

(65) Prior Publication Data

US 2018/0198073 A1 Jul. 12, 2018

Related U.S. Application Data

(63) Continuation of application No. 14/717,454, filed on May 20, 2015, now Pat. No. 9,923,149.

(30) Foreign Application Priority Data

May 23, 2014 (JP) ................................. 2014-106780

(51) Int. Cl.
*C07D 239/26* (2006.01)
*C07D 251/24* (2006.01)
(Continued)

(52) U.S. Cl.
CPC ........ *H01L 51/0067* (2013.01); *C07D 239/26* (2013.01); *C07D 251/24* (2013.01);
(Continued)

(58) Field of Classification Search
CPC .................................................. H01L 51/0067
(Continued)

(56) References Cited

U.S. PATENT DOCUMENTS 6,821,646 B2 11/2004 Tsuboyama et al.
6,838,818 B2 1/2005 Furugori et al.
(Continued)

FOREIGN PATENT DOCUMENTS

CN 001708485 A 12/2005
CN 101353327 A 1/2009
(Continued)

OTHER PUBLICATIONS

Achelle, S. et al., "Star-and Banana-Shaped Oligomers with a Pyrimidine Core:Synthesis and Light-Emitting Properties," European Journal of Organic Chemistry, 2008, pp. 3129-3140.
(Continued)

*Primary Examiner* — Duc Truong
(74) *Attorney, Agent, or Firm* — Husch Blackwell LLP

(57) ABSTRACT

Provided is a novel heterocyclic compound, a novel heterocyclic compound that can be used in a light-emitting element, or a highly reliable light-emitting device, electronic device, and lighting device in each of which the light-emitting element using the novel heterocyclic compound is used. One embodiment of the present invention is a heterocyclic compound represented by General Formula (G1).

(G1)

$$B-Ar\underset{N}{\overset{A^2}{\diagdown}}\overset{Ar}{\diagup}B$$
$$\underset{R^1}{\overset{}{\diagup}}A^1$$

(Continued)

In General Formula (G1), each of $A^1$ and $A^2$ independently represents nitrogen or carbon bonded to hydrogen, and at least one of $A^1$ and $A^2$ represents nitrogen; Ar represents a substituted or unsubstituted arylene group having 6 to 18 carbon atoms; B represents a substituted or unsubstituted fluorenyl group; and $R^1$ represents hydrogen, an alkyl group having 1 to 6 carbon atoms, or an aryl group having 6 to 13 carbon atoms.

7 Claims, 19 Drawing Sheets

(51) Int. Cl.
| | | |
|---|---|---|
| | *H01L 51/00* | (2006.01) |
| | *C09K 11/06* | (2006.01) |
| | *H01L 27/32* | (2006.01) |
| | *H01L 51/50* | (2006.01) |

(52) U.S. Cl.
CPC .......... *C09K 11/06* (2013.01); *H01L 51/0058*
(2013.01); *C09K 2211/1011* (2013.01); *C09K 2211/1044* (2013.01); *H01L 27/3244* (2013.01); *H01L 51/0059* (2013.01); *H01L 51/0072* (2013.01); *H01L 51/0074* (2013.01); *H01L 51/0085* (2013.01); *H01L 51/5012* (2013.01)

(58) Field of Classification Search
USPC .......................................................... 257/4
See application file for complete search history.

(56) References Cited

U.S. PATENT DOCUMENTS

| | | | |
|---|---|---|---|
| 7,166,958 | B2 | 1/2007 | Furugori et al. |
| 7,332,233 | B2 | 2/2008 | Park et al. |
| 7,446,471 | B2 | 11/2008 | Furugori et al. |
| 7,649,077 | B2 | 1/2010 | Craig et al. |
| 7,651,791 | B2 | 1/2010 | Nakano et al. |
| 7,736,758 | B2 | 6/2010 | Furugori et al. |
| 7,790,299 | B2 | 9/2010 | Furugori et al. |
| 7,846,560 | B2 | 12/2010 | Nakano et al. |
| 7,910,227 | B2 | 3/2011 | Furugori et al. |
| 8,012,602 | B2 | 9/2011 | Schafer et al. |
| 8,128,727 | B2 | 3/2012 | Nomura et al. |
| 8,142,911 | B2 | 3/2012 | Kadoma et al. |
| 9,059,411 | B2 | 6/2015 | Suzuki et al. |
| 9,419,237 | B2 | 8/2016 | Shitagaki et al. |
| 9,923,148 | B2 | 3/2018 | Schafer et al. |
| 9,923,149 | B2 * | 3/2018 | Inoue .................. H01L 51/0067 |
| 2002/0063516 | A1 | 5/2002 | Tsuboyama et al. |
| 2006/0008670 | A1 | 1/2006 | Lin et al. |
| 2007/0141387 | A1 | 6/2007 | Nakano et al. |
| 2007/0190355 | A1 | 8/2007 | Ikeda et al. |
| 2010/0019203 | A1 | 1/2010 | Akino et al. |
| 2010/0084971 | A1 | 4/2010 | Nakano et al. |
| 2010/0240892 | A1 | 9/2010 | Schafer et al. |
| 2011/0089821 | A1 | 4/2011 | Furugori et al. |
| 2011/0210316 | A1 | 9/2011 | Kadoma et al. |
| 2012/0098417 | A1 | 4/2012 | Inoue et al. |
| 2012/0126217 | A1 | 5/2012 | Yoshida et al. |
| 2012/0133273 | A1 | 5/2012 | Inoue et al. |
| 2012/0214993 | A1 | 8/2012 | Aihara et al. |
| 2012/0274201 | A1 | 11/2012 | Seo et al. |
| 2012/0277427 | A1 | 11/2012 | Inoue et al. |
| 2013/0048964 | A1 | 2/2013 | Takeda et al. |
| 2013/0221335 | A1 | 8/2013 | Suzuki et al. |
| 2016/0343952 | A1 | 11/2016 | Shitagaki et al. |
| 2018/0269403 | A1 | 9/2018 | Schafer et al. |

FOREIGN PATENT DOCUMENTS

| | | |
|---|---|---|
| CN | 101616986 A | 12/2009 |
| CN | 103570607 A | 2/2014 |
| EP | 2 116 574 A1 | 11/2009 |
| EP | 2 468 731 A1 | 6/2012 |
| JP | 2002-324677 A | 11/2002 |
| JP | 2003-045662 A | 2/2003 |
| JP | 2003-068465 A | 3/2003 |
| JP | 2005-053912 A | 3/2005 |
| JP | 2006-510732 | 3/2006 |
| JP | 2007-123392 A | 5/2007 |
| JP | 2008-214615 A | 9/2008 |
| JP | 2009-158848 A | 7/2009 |
| JP | 2011-063584 A | 3/2011 |
| JP | 2011-084553 A | 4/2011 |
| JP | 2011-121877 A | 6/2011 |
| JP | 2011-121934 A | 6/2011 |
| JP | 2011-126851 A | 6/2011 |
| JP | 2011-201869 A | 10/2011 |
| JP | 2011-219442 A | 11/2011 |
| JP | 2011-219443 A | 11/2011 |
| JP | 2012-097006 A | 5/2012 |
| JP | 2013-209366 A | 10/2013 |
| KR | 2009-0118921 A | 11/2009 |
| KR | 2010-0131745 A | 12/2010 |
| KR | 2011-0130904 A | 12/2011 |
| TW | 200848410 | 12/2008 |
| WO | WO 2004/039786 A1 | 5/2004 |
| WO | WO 2004/039864 A1 | 5/2004 |
| WO | WO 2005/085387 A1 | 9/2005 |
| WO | WO 2008/096735 A1 | 8/2008 |
| WO | WO 2011/021689 A1 | 2/2011 |
| WO | WO 2011/046182 A1 | 4/2011 |
| WO | WO 2011/070992 A1 | 6/2011 |
| WO | WO 2011/149240 A2 | 12/2011 |
| WO | WO 2012/096263 A1 | 7/2012 |

OTHER PUBLICATIONS

Su, S.-J. et al., "RGB Phosphorescent Organic Light-Emitting Diodes by Using Host Materials with Heterocyclic Cores:Effect of Nitrogen Atom Orientations," Chemistry of Materials, 2011, vol. 23, No. 2, pp. 274-284.
Goldsmith, C.R. et al., "C—H Bond Activation by a Ferric Methoxide Complex: Modeling the Rate-Determining Step in the Mechanism of Lipoxygenase," Journal of the American Chemical Society, 2002, vol. 124, No. 1, pp. 83-96.
Onishi, T. et al., "A Method of Measuring an Energy Level," High Molecular EL Materials—Development of Light-Emitting High Molecular Compounds, Dec. 25, 2004, pp. 64-67, Kyoritsu Shuppan.
Ren, S. et al., "Star-Shaped Donor-π-Acceptor Conjugated Oligomers with 1,3,5-Triazine Cores: Convergent Synthesis and Multifunctional Properties," Journal of Physical Chemistry B, Jul. 22, 2010, vol. 114, No. 32, pp. 10374-10383, American Chemical Society.
Zhong, H. et al., "New Conjugated Triazine Based Molecular Materials for Application in Optoelectronic Devices: Design, Synthesis, and Properties," Journal of Physical Chemistry C, Dec. 21, 2010, vol. 115, No. 5, pp. 2423-2427, American Chemical Society.
Chinese Office Action re Application No. CN 201510263858.1, dated Jul. 23, 2018.

* cited by examiner

HETEROCYCLIC COMPOUND, LIGHT-EMITTING ELEMENT, LIGHT-EMITTING DEVICE, ELECTRONIC DEVICE, AND LIGHTING DEVICE

This application is a continuation of U.S. application Ser. No. 14/717,454, filed on May 20, 2015 now U.S. Pat. No. 9,923,149 which is incorporated herein by reference.

BACKGROUND OF THE INVENTION

1. Field of the Invention

The present invention relates to an object, a method, or a fabrication method. In addition, the present invention relates to a process, a machine, manufacture, or a composition of matter. In particular, one embodiment of the present invention relates to a semiconductor device, a display device, a light-emitting device, a driving method thereof, or a fabrication method thereof. In particular, one embodiment of the present invention relates to a heterocyclic compound and a novel method of synthesizing the same. In addition, one embodiment of the present invention relates to a light-emitting element, a light-emitting device, an electronic device, and a lighting device that include the heterocyclic compound.

2. Description of the Related Art

A light-emitting element using an organic compound as a luminous body, which has features such as thinness, lightness, high-speed response, and DC drive at low voltage, is expected to be used in a next-generation flat panel display. In particular, a display device in which light-emitting elements are arranged in a matrix is considered to have advantages in a wide viewing angle and excellent visibility over a conventional liquid crystal display device.

The light emission mechanism is said to be as follows: when a voltage is applied between a pair of electrodes with an electroluminescent layer (an EL layer) including a luminous body provided therebetween, electrons injected from the cathode and holes injected from the anode recombine in the light emission center of the EL layer to form molecular excitons, and energy is released and light is emitted when the molecular excitons return to the ground state. Singlet excitation and triplet excitation are known as excited states, and it is thought that light emission can be obtained through either of the excited states.

An organic compound is mainly used for an EL layer in such a light-emitting element and greatly affects an improvement in the characteristics of the light-emitting element. For this reason, a variety of novel organic compounds have been developed (e.g., Patent Document 1).

REFERENCE

Patent Document

[Patent Document 1] Japanese Published Patent Application No. 2011-201869

SUMMARY OF THE INVENTION

In view of the above, one embodiment of the present invention provides a novel heterocyclic compound. Another embodiment of the present invention provides a novel heterocyclic compound with a stable molecular structure. Another embodiment of the present invention provides a novel heterocyclic compound that can be used in a light-emitting element. Another embodiment of the present invention provides a novel heterocyclic compound that can be used in an electroluminescent layer (an EL layer) of a light-emitting element. Another embodiment of the present invention provides a light-emitting element using the novel heterocyclic compound of one embodiment of the present invention. Another embodiment of the present invention provides a highly reliable light-emitting device, electronic device, and lighting device in each of which the light-emitting element using the novel heterocyclic compound of one embodiment of the present invention is used. Another embodiment of the present invention provides a novel light-emitting element, a novel light-emitting device, a novel lighting device, or the like. Note that the description of these objects does not disturb the existence of other objects. In one embodiment of the present invention, there is no need to achieve all the objects. Other objects will be apparent from and can be derived from the description of the specification, the drawings, the claims, and the like.

One embodiment of the present invention is a compound in which a heterocyclic skeleton is bonded to a fluorene skeleton through an arylene group.

One embodiment of the present invention is a heterocyclic compound represented by General Formula (G1).

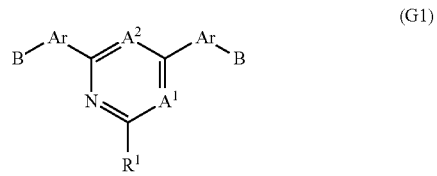

(G1)

In General Formula (G1), each of $A^1$ and $A^2$ independently represents nitrogen or carbon bonded to hydrogen, and at least one of $A^1$ and $A^2$ represents nitrogen; Ar represents a substituted or unsubstituted arylene group having 6 to 18 carbon atoms; B represents a substituted or unsubstituted fluorenyl group; and $R^1$ represents hydrogen, an alkyl group having 1 to 6 carbon atoms, or an aryl group having 6 to 13 carbon atoms.

Another embodiment of the present invention is a heterocyclic compound represented by General Formula (G1) in which B is a substituted or unsubstituted 2-fluorenyl group.

Another embodiment of the present invention is a heterocyclic compound represented by General Formula (G1) in which B is represented by General Formula (α).

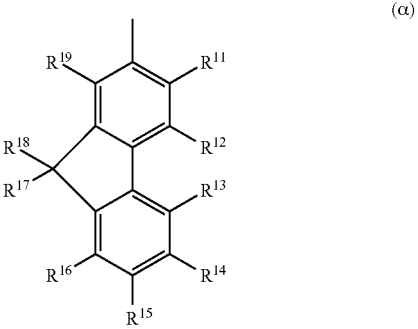

(α)

In General Formula (α), each of $R^{11}$ to $R^{19}$ independently represents hydrogen, an alkyl group having 1 to 6 carbon atoms, or an aryl group having 6 to 12 carbon atoms.

Another embodiment of the present invention is a heterocyclic compound represented by General Formula (G1) in which B is represented by General Formula (β).

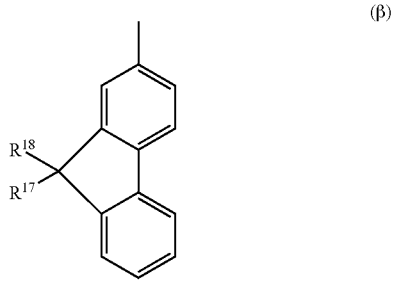

(β)

In General Formula (β), each of $R^{17}$ and $R^{18}$ independently represents hydrogen, an alkyl group having 1 to 6 carbon atoms, or an aryl group having 6 to 12 carbon atoms.

Note that Ar in General Formula (G1) represents a substituted or unsubstituted arylene group having 6 to 18 carbon atoms, such as a phenylene group or a biphenylene group. Examples of the alkyl group having 1 to 6 carbon atoms in General Formula (α), General Formula (β), and General Formula (G1) are a methyl group, an ethyl group, a propyl group, an isopropyl group, and a butyl group. Examples of the aryl group having 6 to 12 carbon atoms in General Formula (α) and General Formula (β) are a phenyl group, a naphthyl group, and a biphenyl group.

Another embodiment of the present invention is a heterocyclic compound represented by Structural Formula (100).

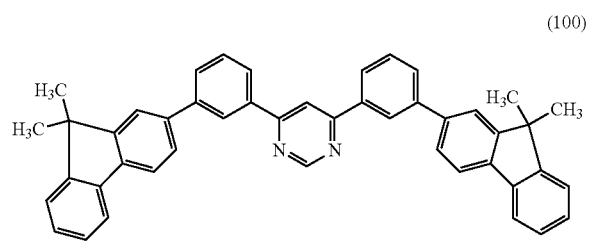 [SMILES: CC1(C)c2ccccc2-c2ccc(-c3cccc(-c4cc(-c5cccc(-c6ccc7c(c6)C(C)(C)c6ccccc6-7)c5)ncn4)c3)cc21]

(100)

Another embodiment of the present invention is a heterocyclic compound represented by Structural Formula (109).

Another embodiment of the present invention is a light-emitting element including any of the heterocyclic compounds with the above structures.

Another embodiment of the present invention is a light-emitting device including the above-described light-emitting element and at least one of a transistor and a substrate.

Note that one embodiment of the present invention includes not only a light-emitting device including the light-emitting element but also an electronic device and a lighting device each using the light-emitting device.

Accordingly, another embodiment of the present invention is an electronic device including the light-emitting device and at least one of a microphone, a camera, an operation button, an external connection portion, and a speaker. Another embodiment of the present invention is an electronic device including the light-emitting device and at least one of a housing, a cover, and a support base.

The light-emitting device in this specification refers to an image display device and a light source (e.g., a lighting device). In addition, the light-emitting device includes, in its category, all of a module in which a light-emitting device is connected to a connector such as a flexible printed circuit (FPC), a tape carrier package (TCP), a module in which a printed wiring board is provided on the tip of a TCP, and a module in which an integrated circuit (IC) is directly mounted on a light-emitting element by a chip on glass (COG) method.

One embodiment of the present invention can provide a novel heterocyclic compound. The novel heterocyclic compound of one embodiment of the present invention has a structure in which a heterocyclic skeleton (a pyrimidine skeleton or a triazine skeleton) is bonded to a fluorene skeleton through an arylene group. A fluorene derivative, which is a reaction intermediate of the novel heterocyclic compound of one embodiment of the present invention, can be highly purified, whereby synthesis using this reaction intermediate can provide a highly purified heterocyclic compound. In addition, since the heterocyclic compound having a fluorene skeleton has a high solubility in an organic solvent, impurities can be reduced by purification using the solvent; thus, a highly purified heterocyclic compound can be obtained. With the use of the highly purified heterocyclic compound as an EL material, a highly reliable and novel light-emitting element, light-emitting device, electronic device, or lighting device can be obtained. Note that the description of these effects does not disturb the existence of other effects. One embodiment of the present invention does not necessarily have all the effects listed above. Other effects will be apparent from and can be derived from the description of the specification, the drawings, the claims, and the like.

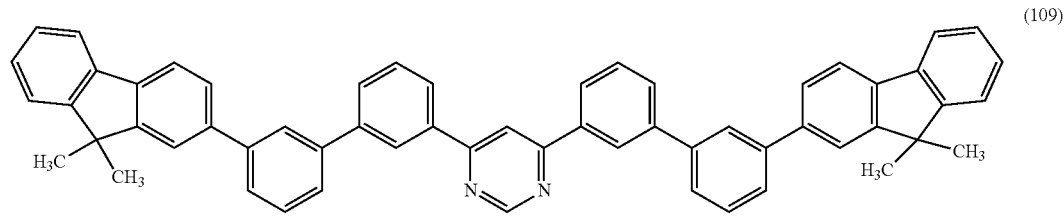 [SMILES: CC1(C)c2ccccc2-c2ccc(-c3cccc(-c4cccc(-c5cc(-c6cccc(-c7cccc(-c8ccc9c(c8)C(C)(C)c8ccccc8-9)c7)c6)ncn5)c4)c3)cc21]

(109)

Figure 3A:
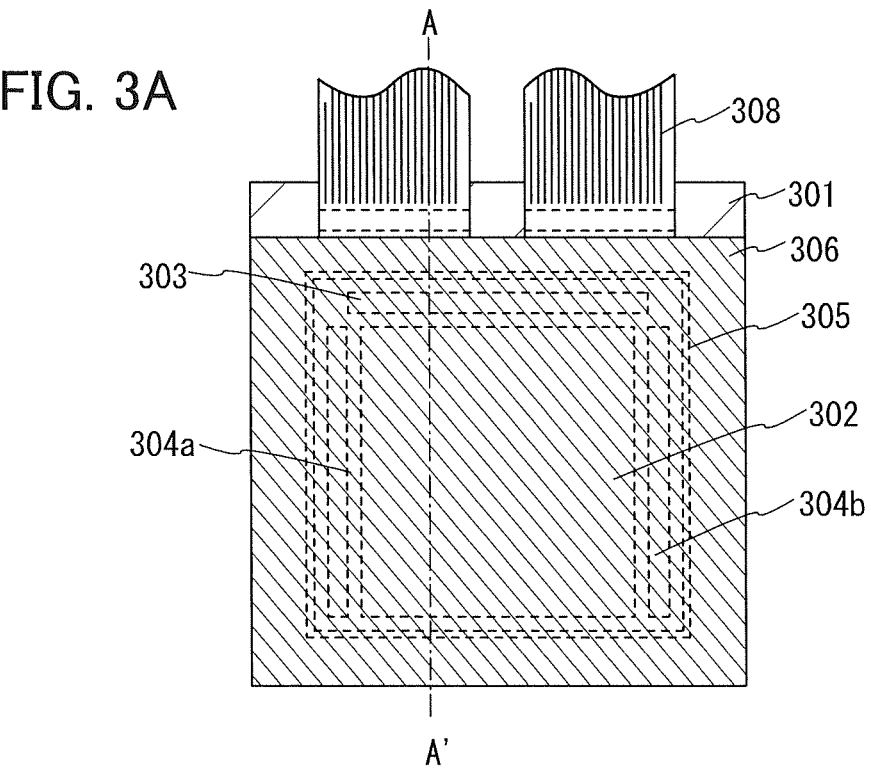
Figure 3B:
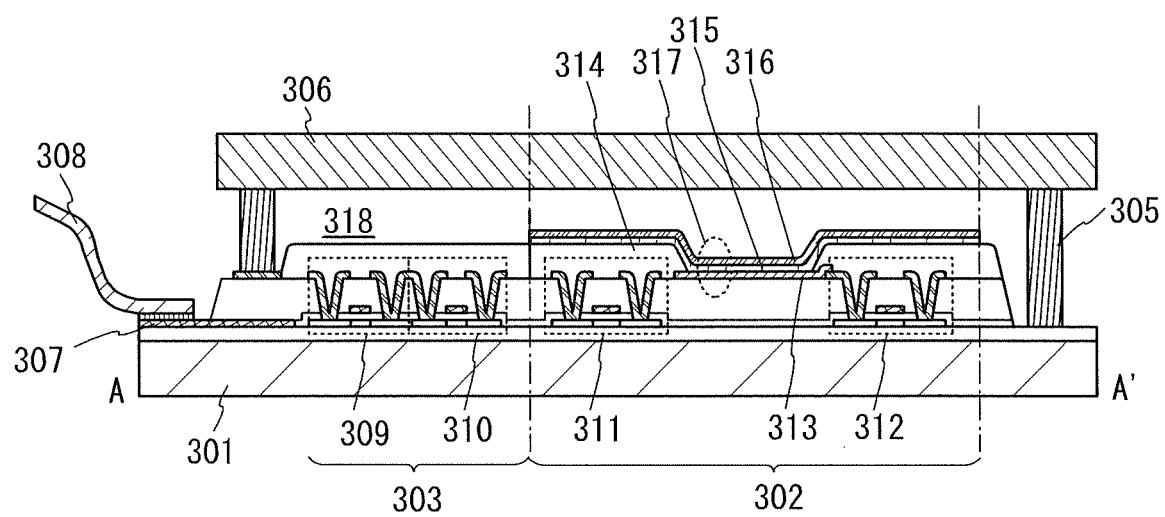

FIGS. 3A and 3B illustrate a light-emitting device.
FIGS. 4A, 4B, 4C, 4D, 4D'1, and 4D'2 illustrate electronic devices.

Figure 5A:
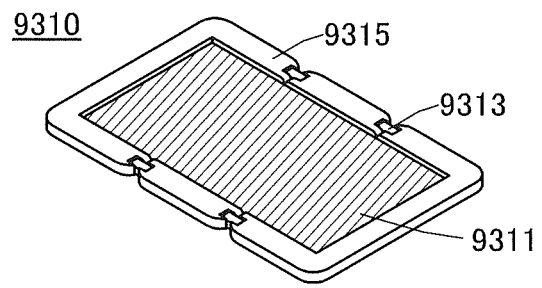
Figure 5B:
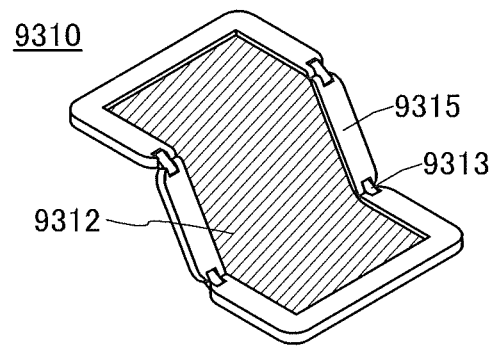
Figure 5C:
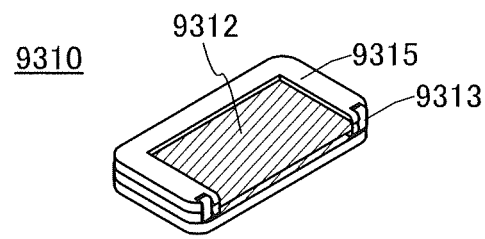

FIGS. 5A to 5C illustrate an electronic device.

Figure 6:
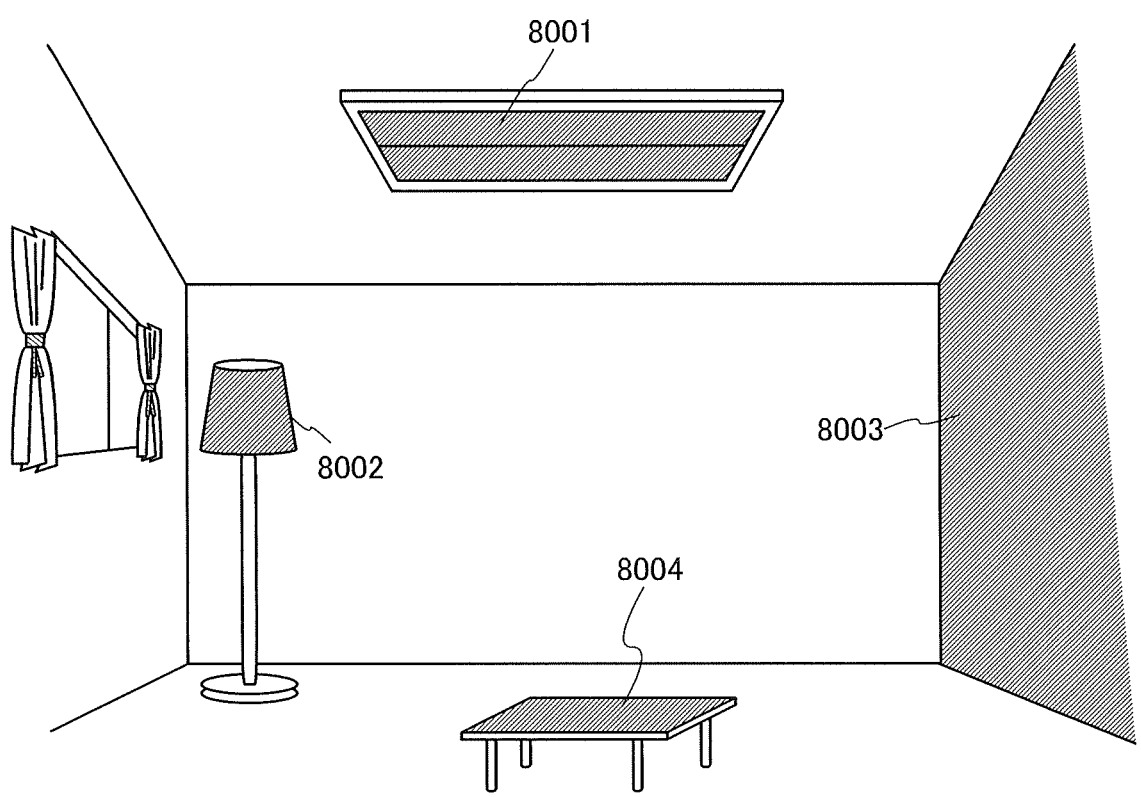

FIG. 6 illustrates lighting devices.

Figure 7:
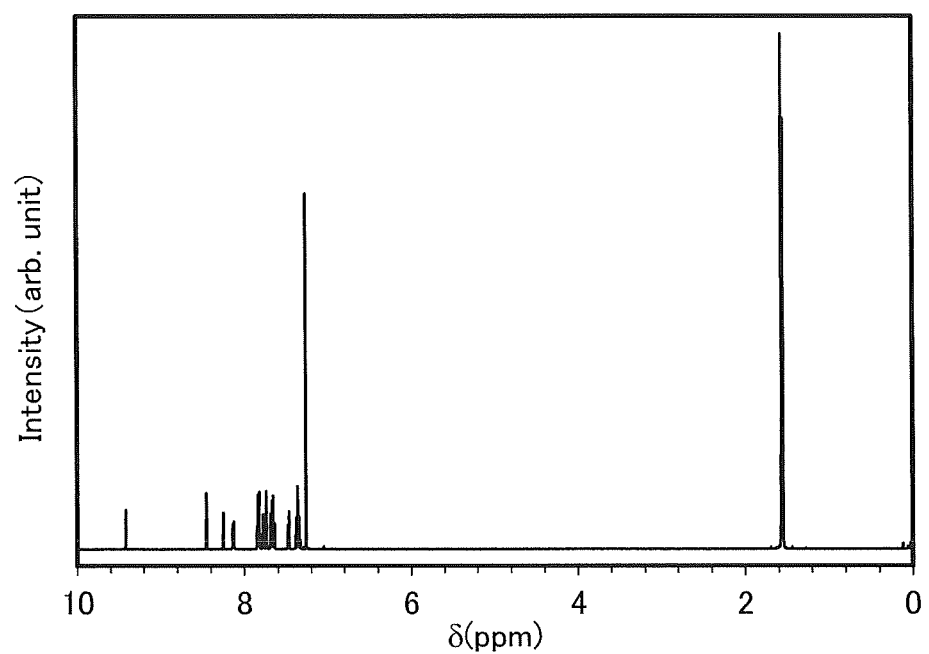

FIG. 7 is a $^1$H-NMR chart of a heterocyclic compound represented by Structural Formula (100).

Figure 8:
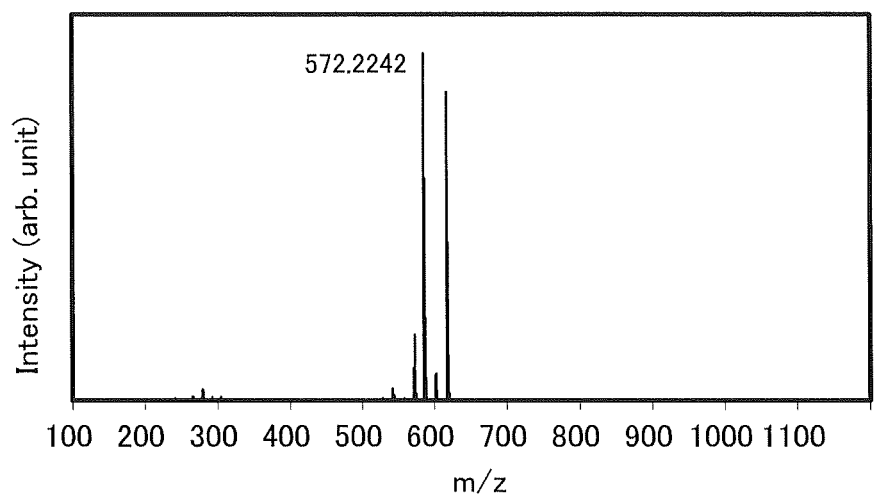

FIG. 8 shows the result of LC-MS measurement of the heterocyclic compound represented by Structural Formula (100).

Figure 9A:
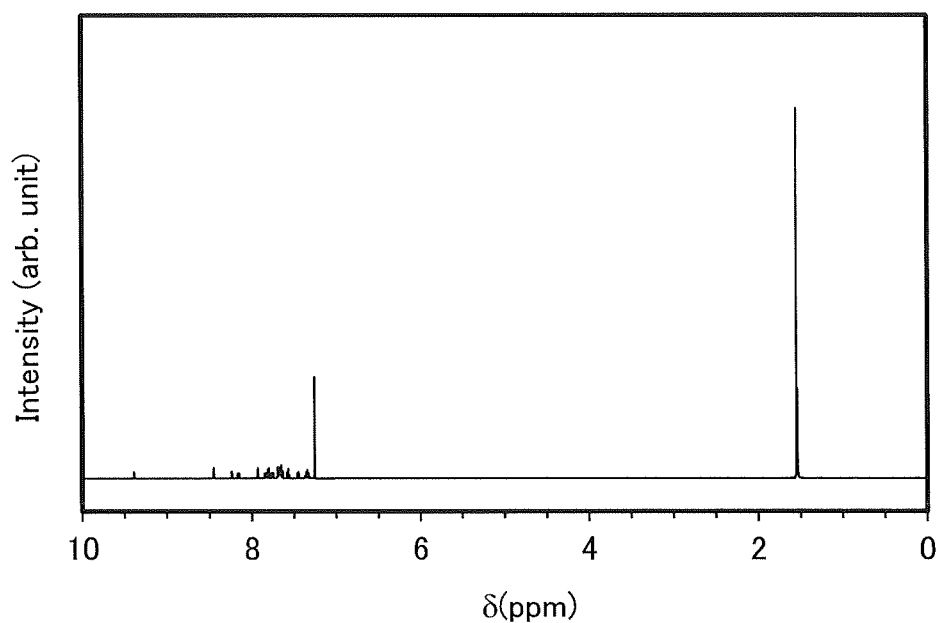
Figure 9B:
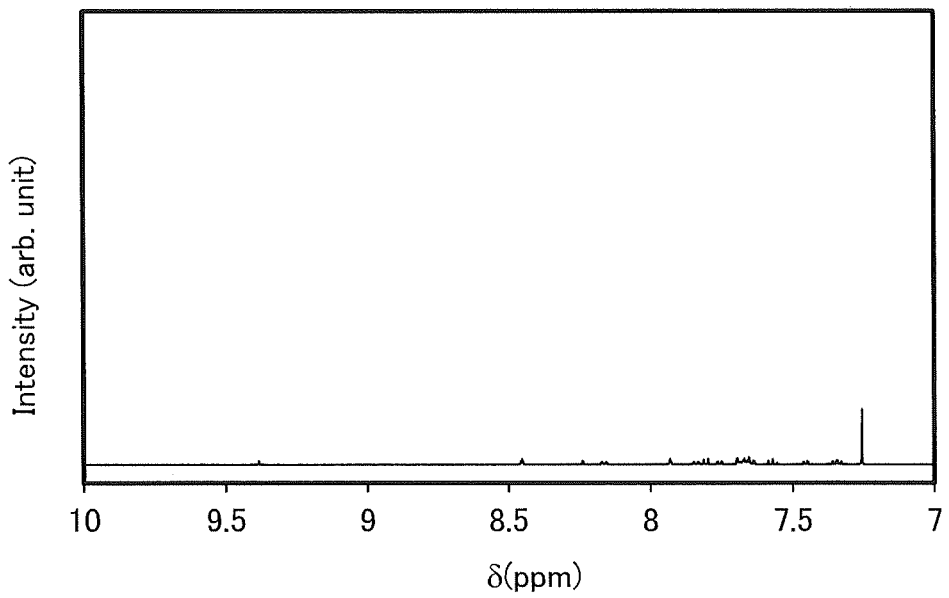

FIGS. 9A and 9B are $^1$H-NMR charts of a heterocyclic compound represented by Structural Formula (109).

Figure 10:
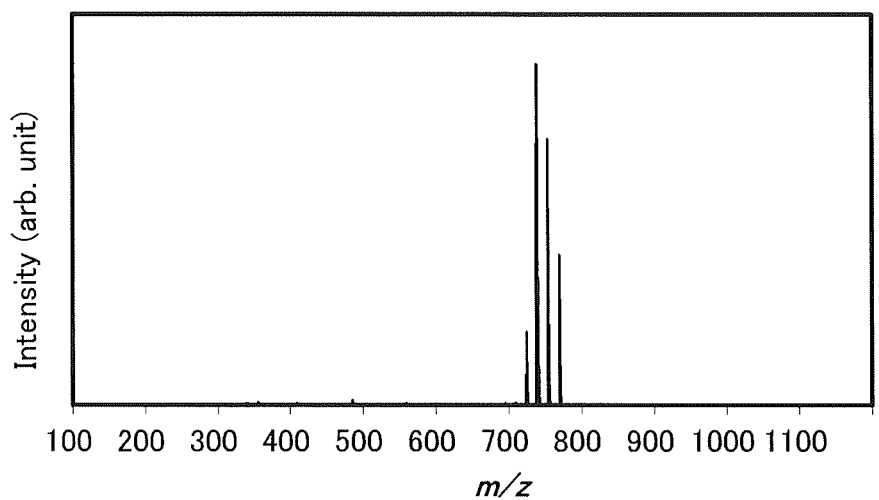

FIG. 10 shows the result of LC-MS measurement of the heterocyclic compound represented by Structural Formula (109).

Figure 11:
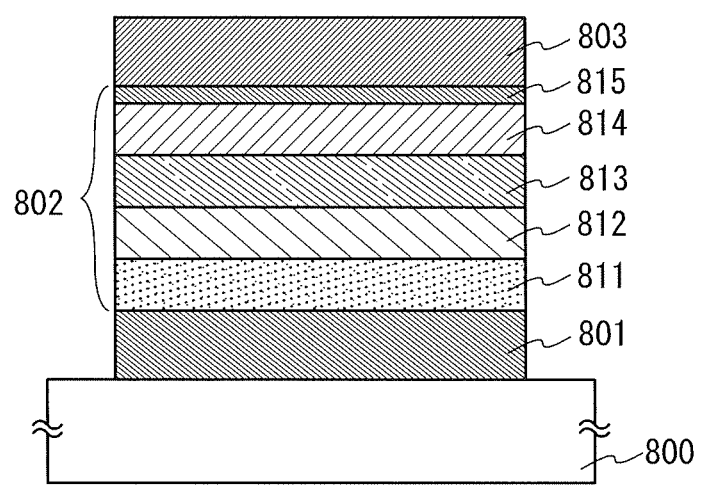

FIG. 11 illustrates a structure of a light-emitting element of Example 3.

Figure 12:
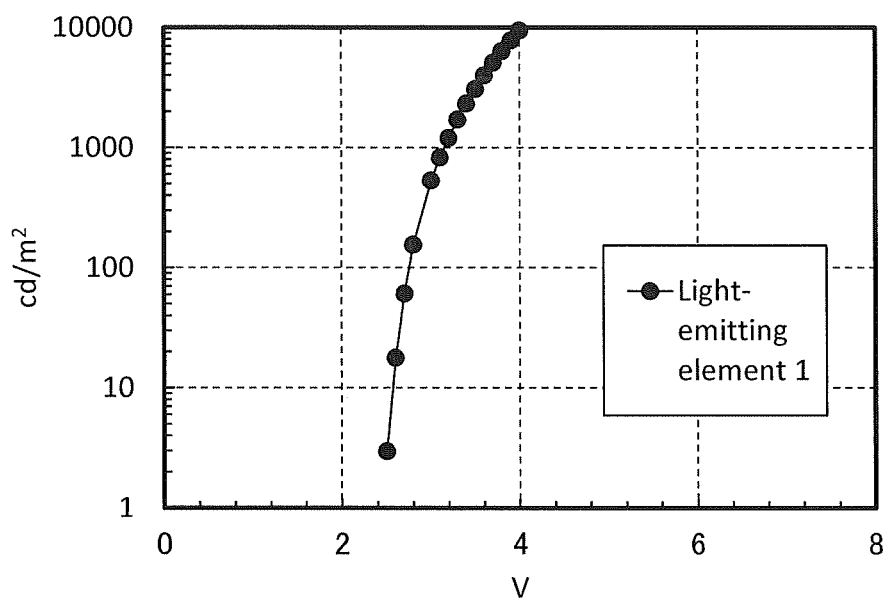

FIG. 12 shows the voltage-luminance characteristics of Light-emitting element 1.

Figure 13:
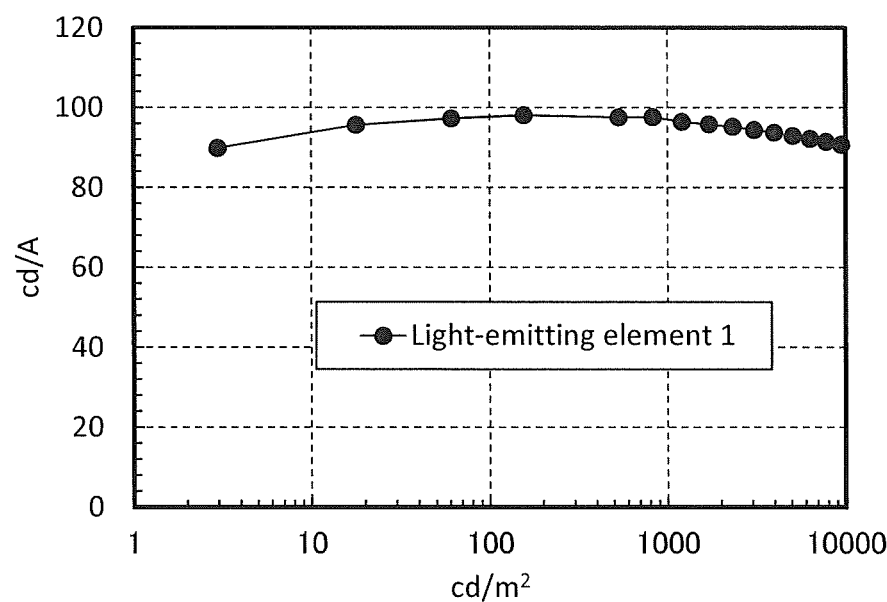

FIG. 13 shows the luminance-current efficiency characteristics of Light-emitting element 1.

Figure 14:
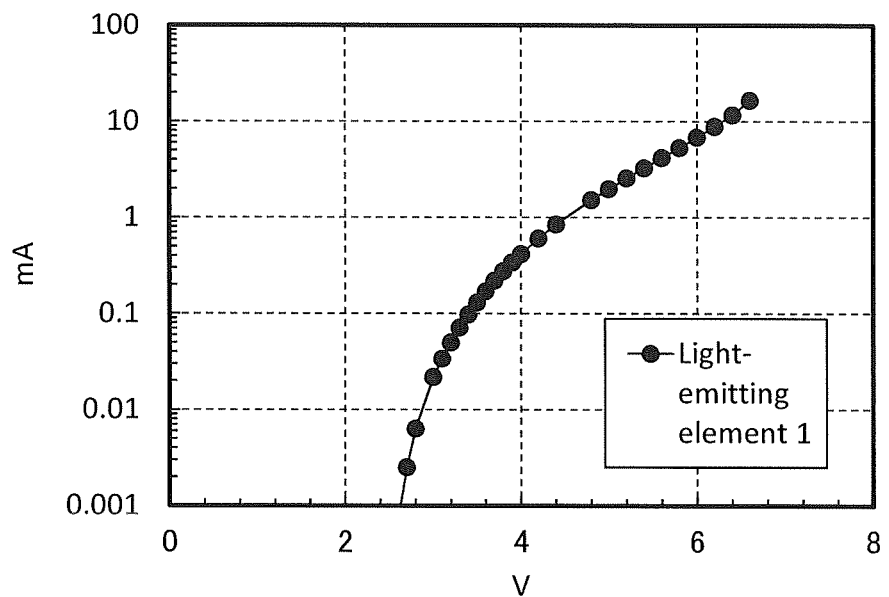

FIG. 14 shows the voltage-current characteristics of Light-emitting element 1.

Figure 15:
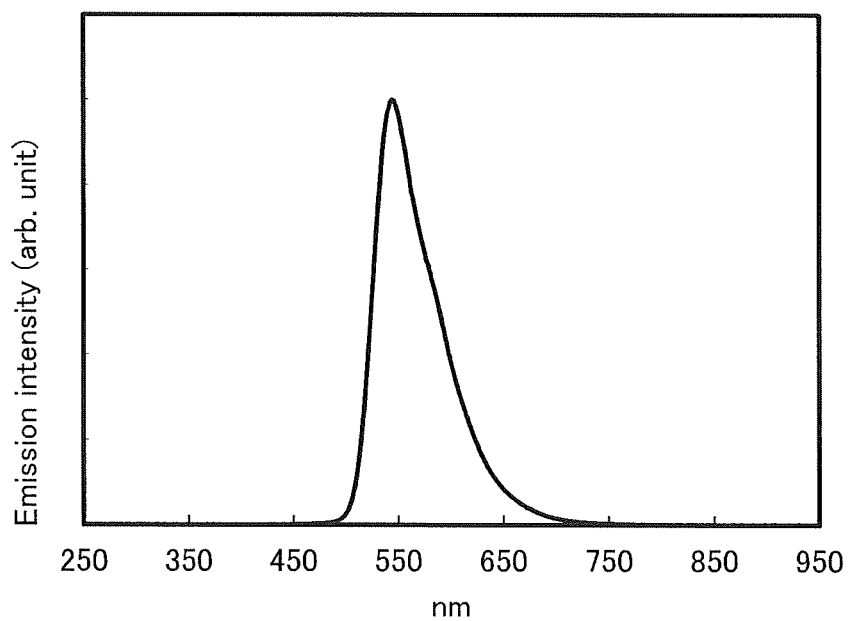

FIG. 15 shows an emission spectrum of Light-emitting element 1.

Figure 16:
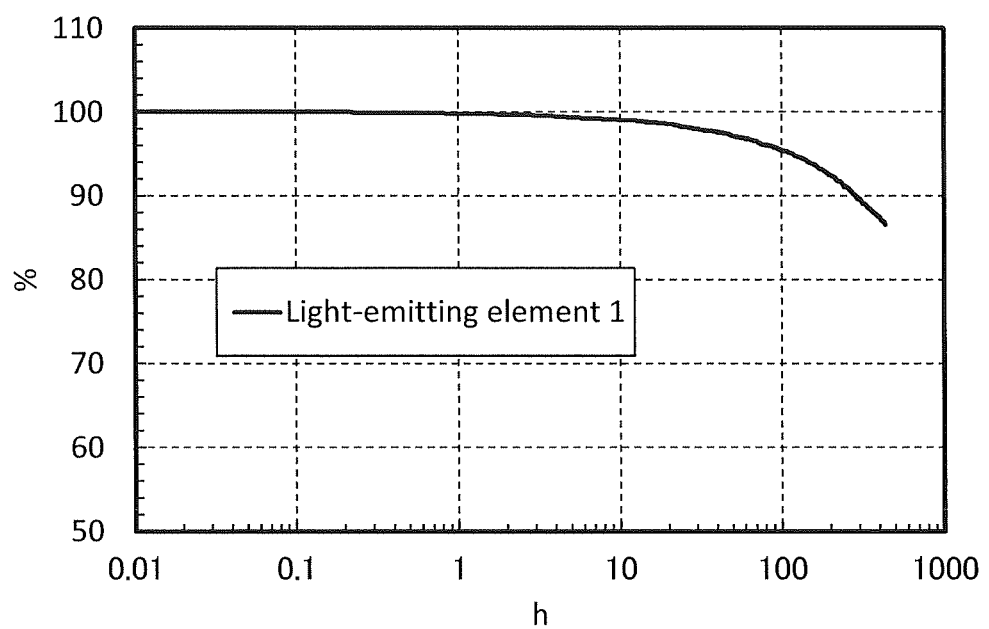

FIG. 16 shows the reliability of Light-emitting element 1.

Figure 17:
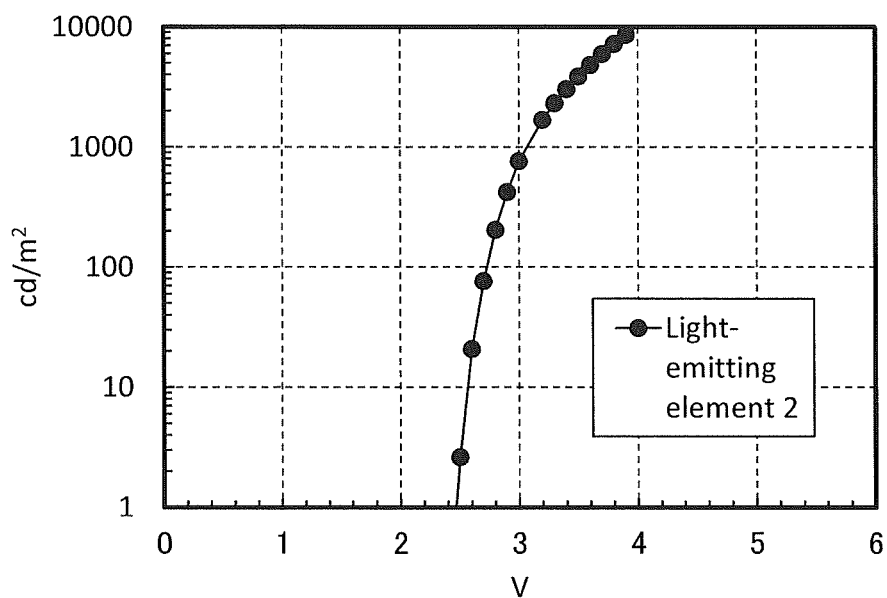

FIG. 17 shows the voltage-luminance characteristics of Light-emitting element 2.

Figure 18:
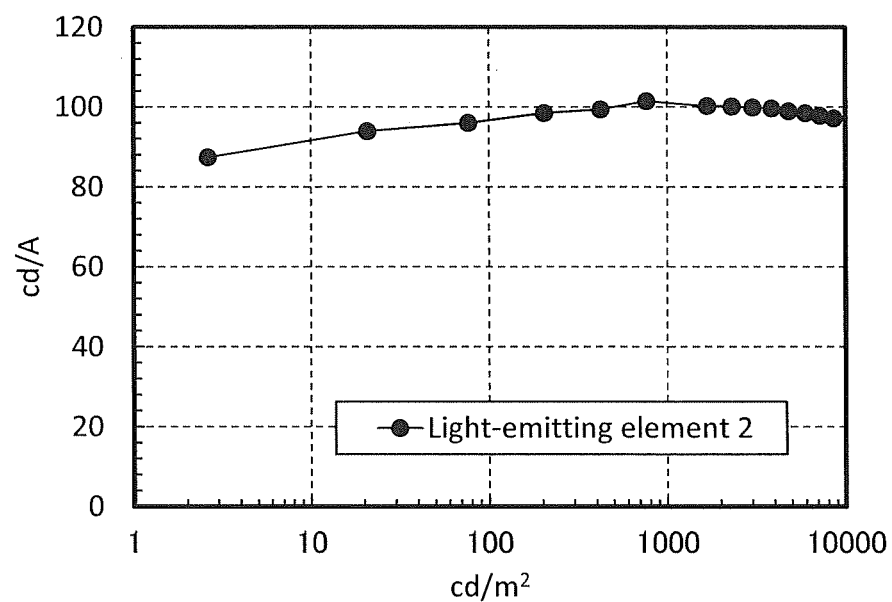

FIG. 18 shows the luminance-current efficiency characteristics of Light-emitting element 2.

Figure 19:
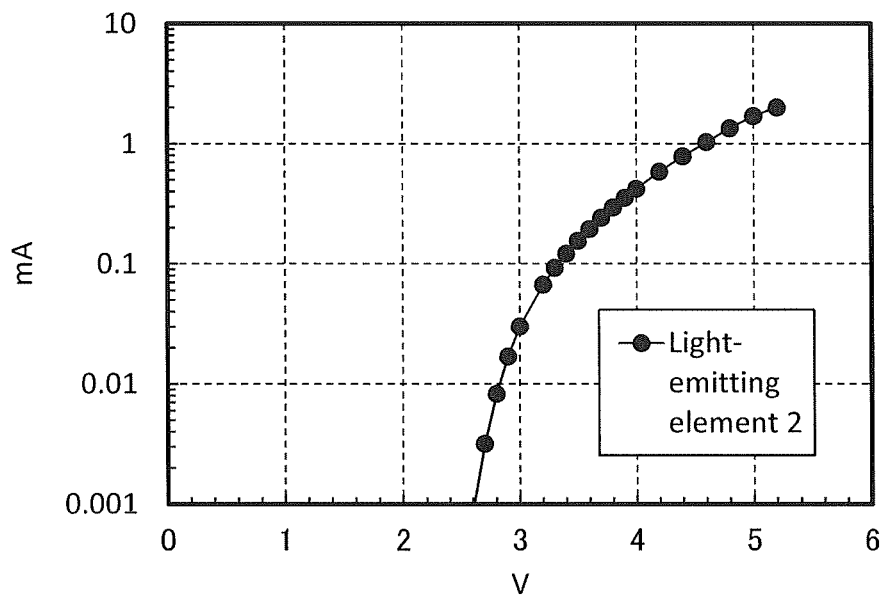

FIG. 19 shows the voltage-current characteristics of Light-emitting element 2.

Figure 20:
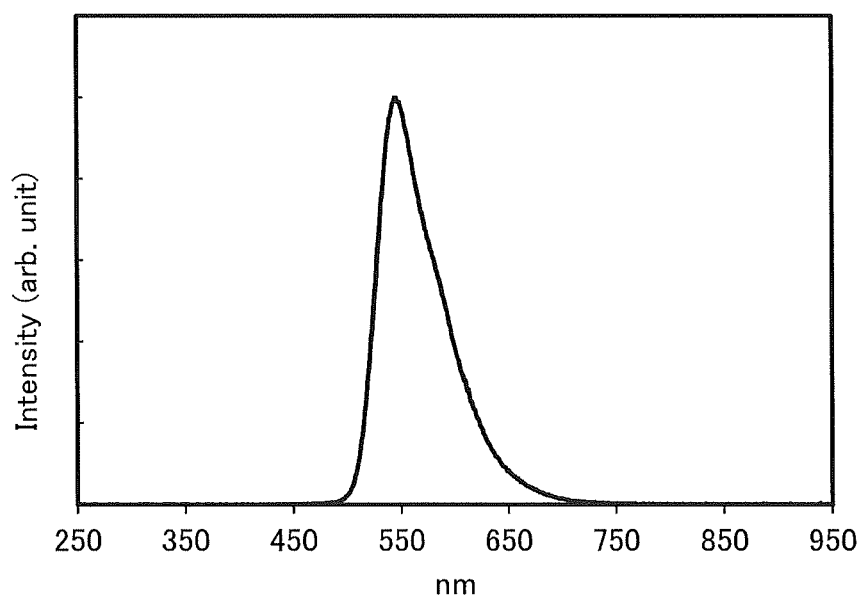

FIG. 20 shows an emission spectrum of Light-emitting element 2.

Figure 21:
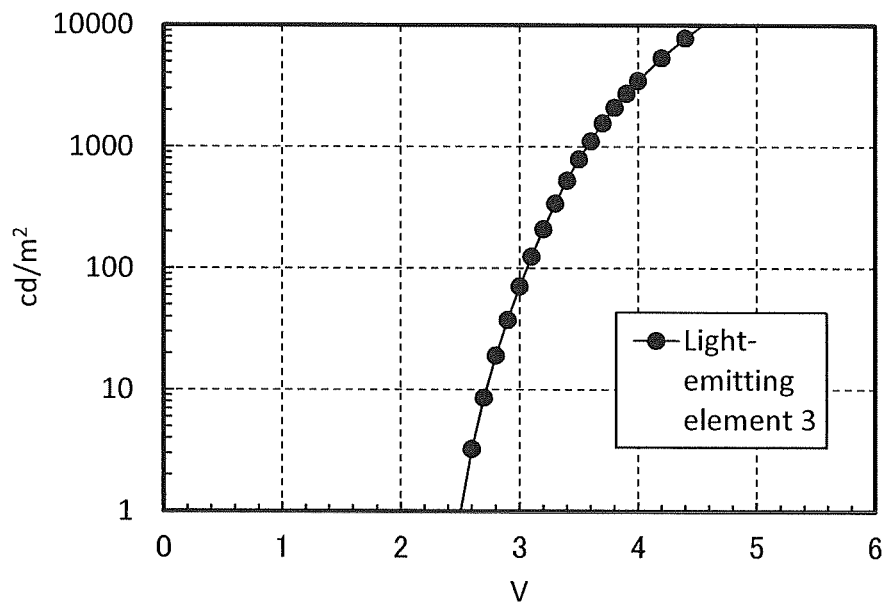

FIG. 21 shows the voltage-luminance characteristics of Light-emitting element 3.

Figure 22:
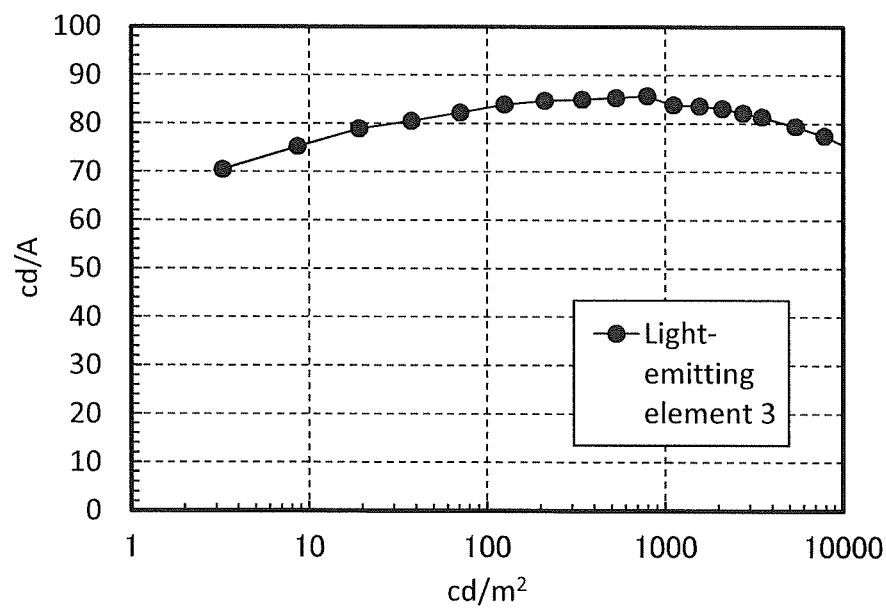

FIG. 22 shows the luminance-current efficiency characteristics of Light-emitting element 3.

Figure 23:
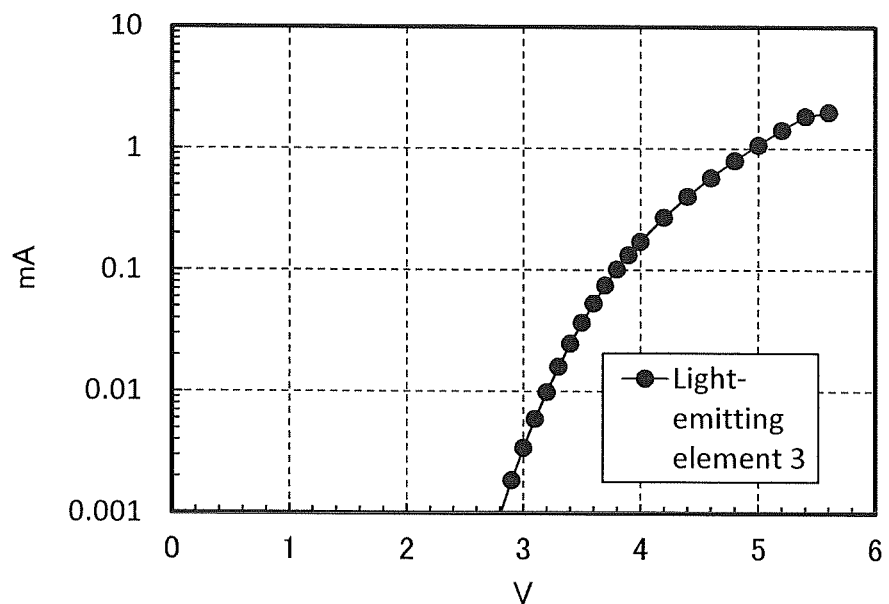

FIG. 23 shows the voltage-current characteristics of Light-emitting element 3.

Figure 24:
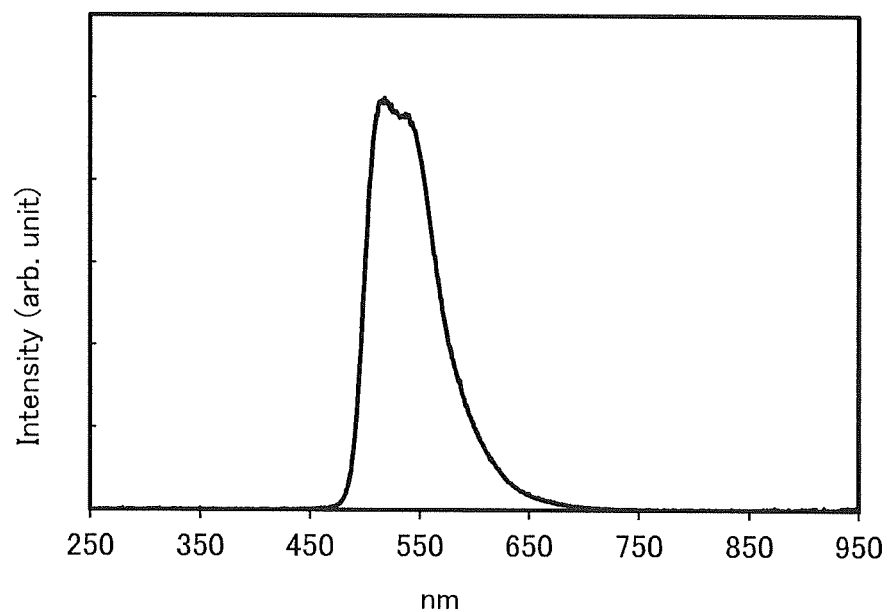

FIG. 24 shows an emission spectrum of Light-emitting element 3.

Figure 25:
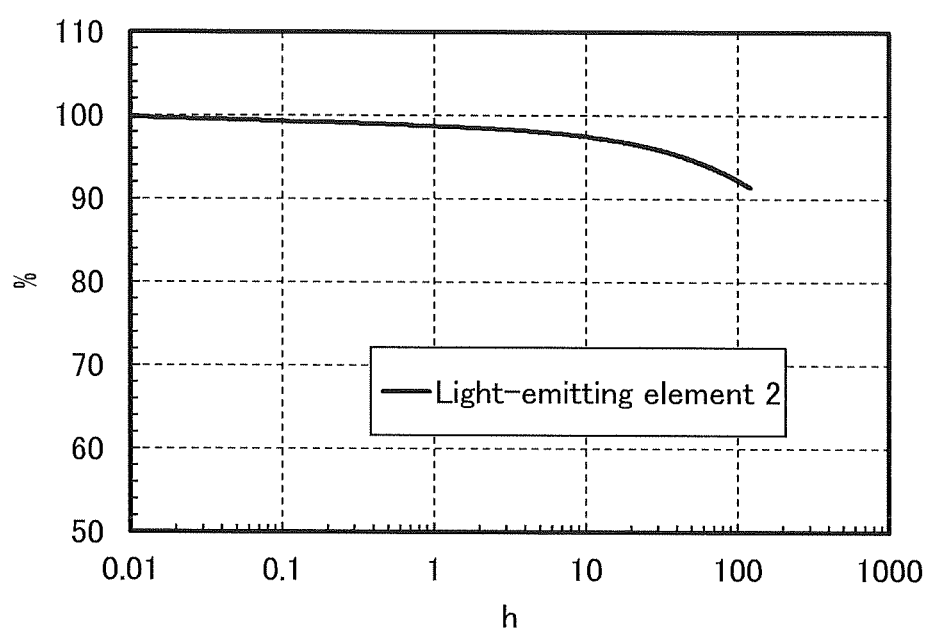

FIG. 25 shows the reliability of Light-emitting element 2.

DETAILED DESCRIPTION OF THE INVENTION

Hereinafter, embodiments of the present invention will be described with reference to the accompanying drawings. Note that the present invention is not limited to the following description, and modes and details thereof can be variously modified without departing from the spirit and scope of the present invention. Therefore, the present invention should not be construed as being limited to the description in the following embodiments.

Embodiment 1

In this embodiment, heterocyclic compounds each of which is one embodiment of the present invention are described. Note that the heterocyclic compound of one embodiment of the present invention is a compound in which a heterocyclic skeleton (a pyrimidine skeleton or a triazine skeleton) is bonded to a fluorene skeleton through an arylene group.

One embodiment of the present invention is a heterocyclic compound represented by General Formula (G1).

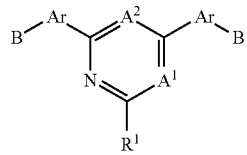

(G1)

In General Formula (G1), each of $A^1$ and $A^2$ independently represents nitrogen or carbon bonded to hydrogen, and at least one of $A^1$ and $A^2$ represents nitrogen; Ar represents a substituted or unsubstituted arylene group having 6 to 18 carbon atoms; B represents a substituted or unsubstituted fluorenyl group; and $R^1$ represents hydrogen, an alkyl group having 1 to 6 carbon atoms, or an aryl group having 6 to 13 carbon atoms.

Another embodiment of the present invention is a heterocyclic compound represented by General Formula (G1) in which B is a substituted or unsubstituted 2-fluorenyl group.

Another embodiment of the present invention is a heterocyclic compound represented by General Formula (G1) in which B is represented by General Formula (α).

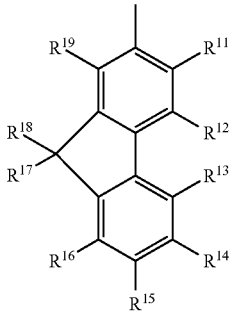

(α)

In General Formula (α), each of $R^{11}$ to $R^{19}$ independently represents hydrogen, an alkyl group having 1 to 6 carbon atoms, or an aryl group having 6 to 12 carbon atoms.

Another embodiment of the present invention is a heterocyclic compound represented by General Formula (G1) in which B is represented by General Formula (β).

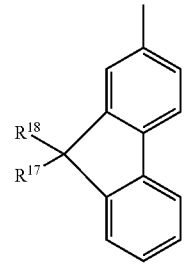

(β)

In General Formula (β), each of $R^{17}$ and $R^{18}$ independently represents hydrogen, an alkyl group having 1 to 6 carbon atoms, or an aryl group having 6 to 12 carbon atoms.

Note that Ar in General Formula (G1) represents a substituted or unsubstituted arylene group having 6 to 18 carbon atoms, such as a phenylene group or a biphenylene group. Specific examples are a 1,2-phenylene group, a 1,3-phenylene group, a 1,4-phenylene group, a 2,6-toluylene group, a 3,5-toluylene group, a 2,4-toluylene group, a 4,6-dimethylbenzene-1,3-diyl group, a 2,4,6-trimethylbenzene-1,3-diyl group, a 2,3,5,6-tetramethylbenzene-1,4-diyl group, a 3,3'-biphenylene group, a 3,4'-biphenylene group, a 4,4'-biphenylene group, a 1,1': 3',1''-terbenzene-3,3''-diyl group, a 1,1': 4',1''-terbenzene-3,3''-diyl group, a 1,1': 4',1''-terbenzene-4, 4''-diyl group, a 1,4-naphthylene group, a 1,5-naphthylene group, a 2,6-naphthylene group, a 2,7-naphthylene group, a 2,7-fluorenylene group, a 9,9-dimethyl-2,7-fluorenylene group, a 9,9-diphenyl-2,7-fluorenylene group, a 9,9-dimethyl-1,4-fluorenylene group, a spiro-9,9'-bifluorene-2,7-diyl group, a 9,10-dihydro-2,7-phenanthrenylene group, a 2,7-phenanthrenylene group, a 3,6-phenanthrenylene group, and a 9,10-phenanthrenylene group. Note that the bonding position is not limited if bonding is possible.

Furthermore, specific examples of the alkyl group having 1 to 6 carbon atoms in the above general formulae (α), (β), and (G1) are a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, a 2,3-dimethylbutyl group, and the like.

Specific examples of the aryl group having 6 to 12 carbon atoms in the above general formulae (α), (β), and (G1) are a phenyl group, a naphthyl group, a biphenyl group, and the like. Note that there is no limitation on the bonding position.

The following will show examples of methods of synthesizing a heterocyclic compound represented by the above General Formula (G1), as an example of a method of synthesizing a fluorene compound of one embodiment of the present invention.

<<Synthesis Method of Heterocyclic Compound Represented by General Formula (G1)>>

The heterocyclic compound represented by General Formula (G1) can be synthesized by a simple synthesis scheme as follows. For example, as shown in Synthesis Scheme (a), the heterocyclic compound can be obtained by reacting a halogen compound of a pyrimidine or triazine derivative (A1) with an arylboronic acid compound to which a fluorene derivative is bonded (A2).

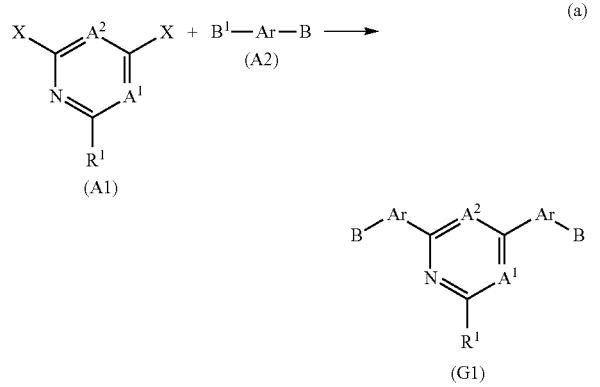

Alternatively, the heterocyclic compound represented by General Formula (G1) may be obtained in such a manner that a pyrimidine or triazine derivative to which an aryl group is bonded (B1) may be reacted with a boronic acid compound of a fluorene derivative (B2) as shown in Scheme (b).

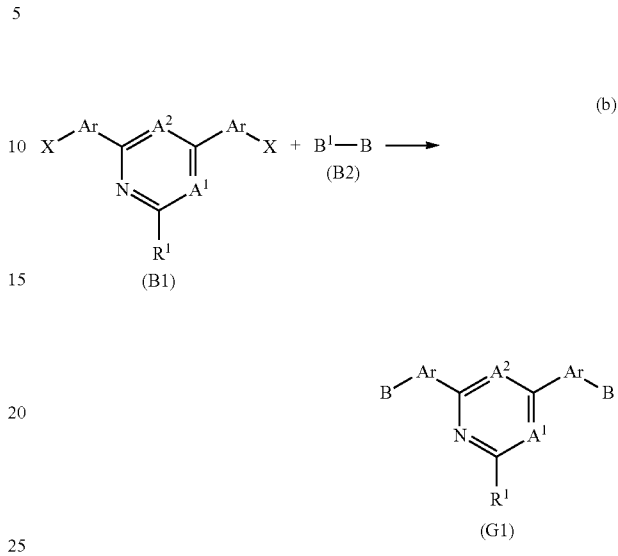

In Synthesis Schemes (a) and (b), each of $A^1$ and $A^2$ independently represents nitrogen or carbon bonded to hydrogen, and at least one of $A^1$ and $A^2$ represents nitrogen; Ar represents a substituted or unsubstituted arylene group having 6 to 18 carbon atoms; B represents a substituted or unsubstituted fluorenyl group; $B^1$ represents a boronic acid, a boronic ester, a cyclic-triolborate salt, or the like, and as the cyclic-triolborate salt, a lithium salt, a potassium salt, or a sodium salt may be used; $R^1$ represents hydrogen, an alkyl group having 1 to 6 carbon atoms, or an aryl group having 6 to 13 carbon atoms; and X represents halogen, and specifically, chlorine, bromine, or iodine is preferred as the halogen. In Synthesis Schemes (a) and (b), a known catalyst such as a palladium catalyst can be used. As the solvent, alcohol such as toluene, xylene, or ethanol, or a mixture thereof can be used.

Alternatively, although the scheme is not shown here, a boronic acid compound of a pyrimidine derivative or a boronic acid compound of a triazine derivative may be reacted with a halogen compound of a fluorene derivative.

Since various kinds of compounds are available commercially or can be synthesized as the compounds (A1), (A2), (B1), and (B2) in Synthesis Schemes (a) and (b), many kinds of heterocyclic compounds can be synthesized as the heterocyclic compound represented by General Formula (G1). Thus, a feature of the heterocyclic compound of one embodiment of the present invention is an abundance of variations.

The above is the description of the example of a method of synthesizing the heterocyclic compound of one embodiment of the present invention; however, the present invention is not limited thereto and any other synthesis method may be employed.

Specific structural formulae of the heterocyclic compound (General Formula (G1)) of one embodiment of the present invention are shown below (Structural Formulae (100) to (123)). Note that one embodiment of the present invention is not limited thereto.

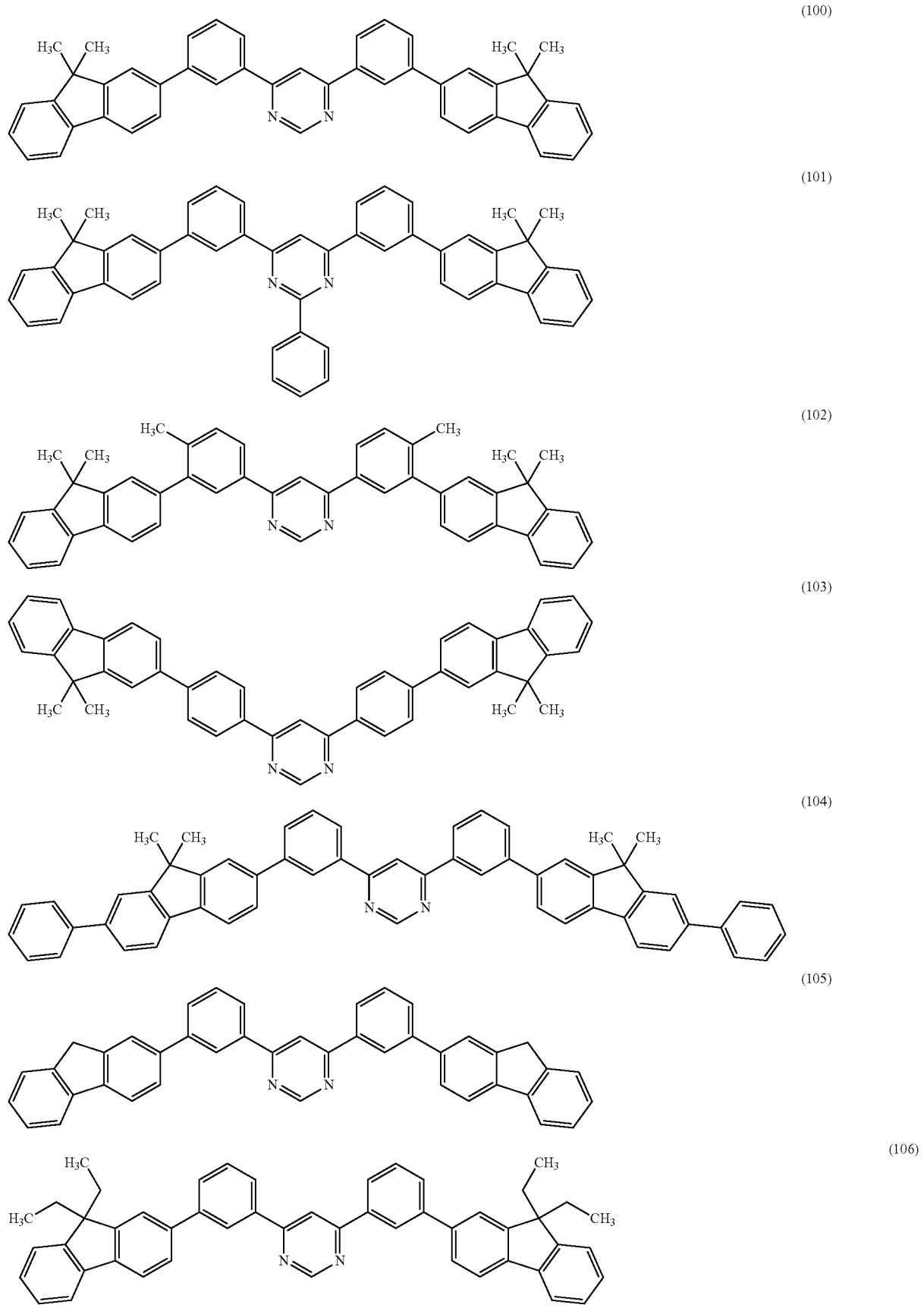

-continued
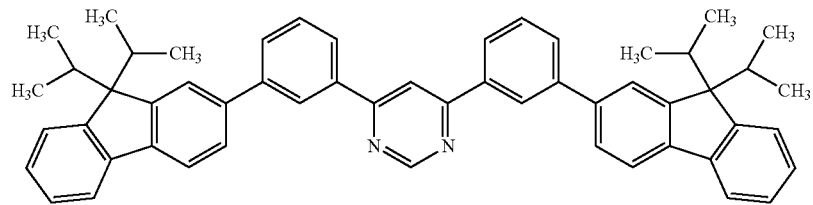
(107)
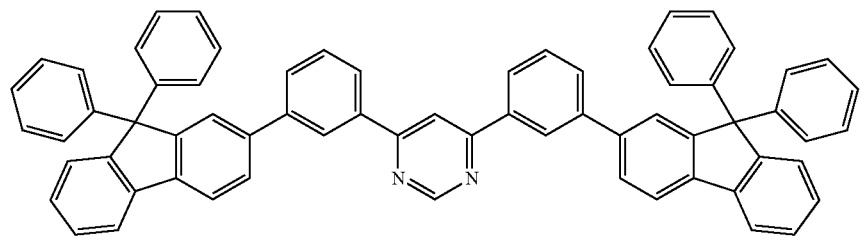
(108)
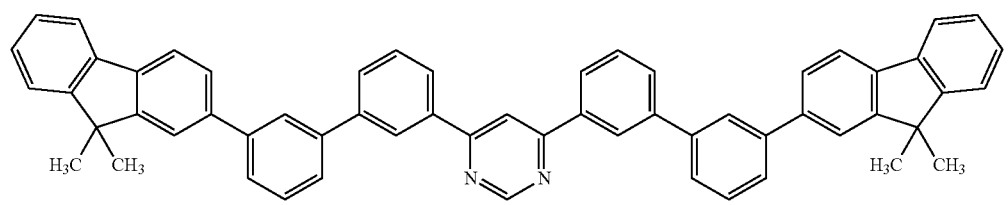
(109)
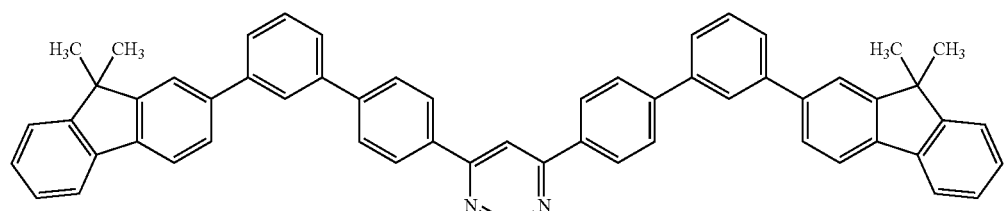
(110)
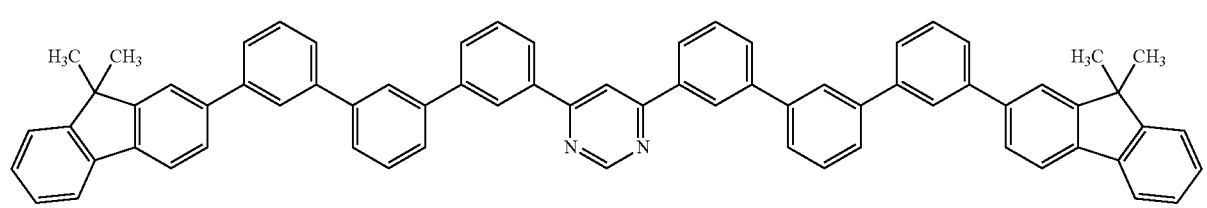
(111)
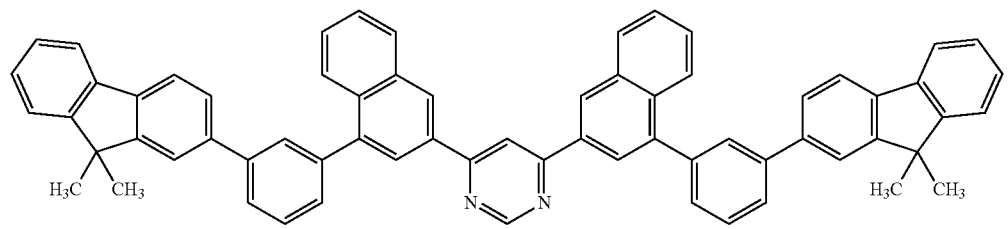
(112)
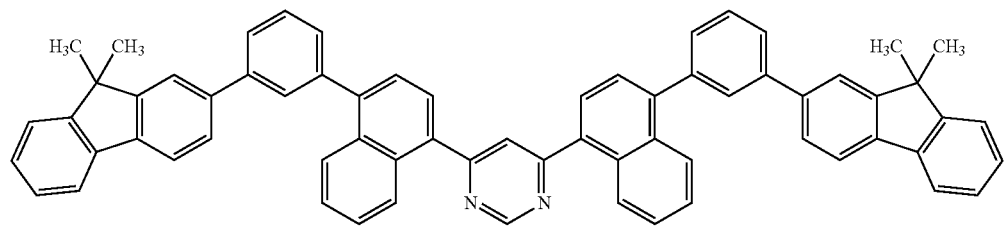
(113)

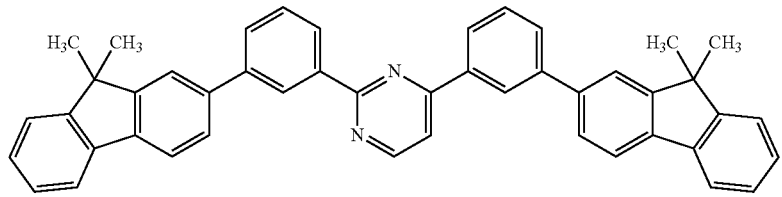
(114)
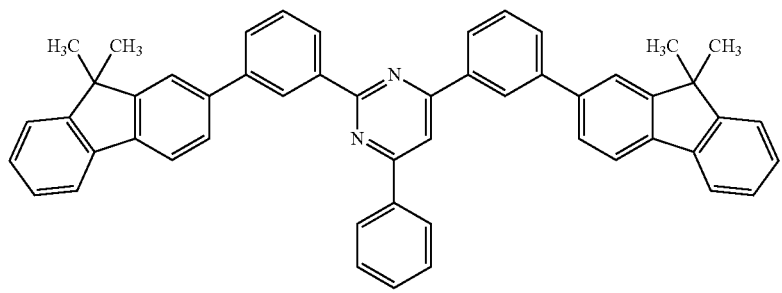
(115)
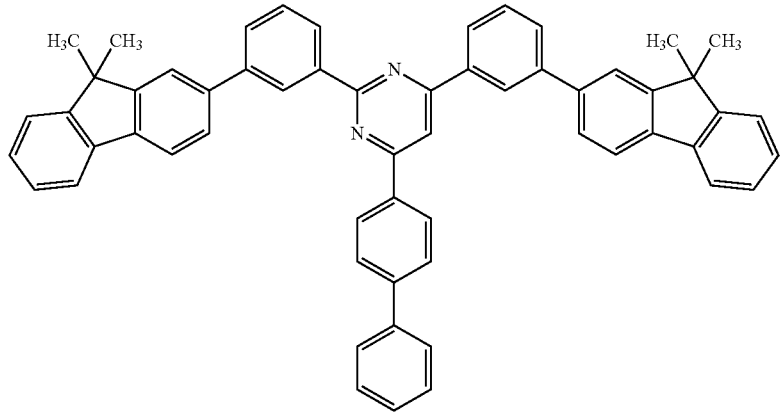
(116)
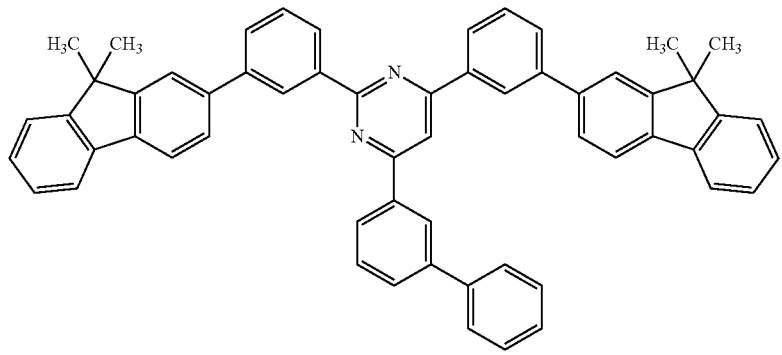
(117)

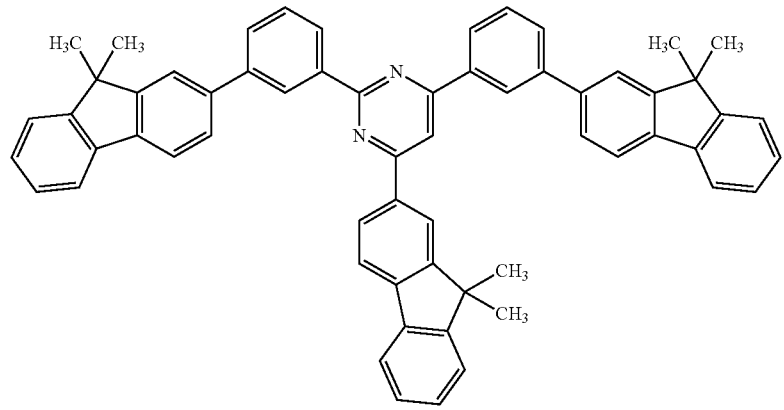
(118)
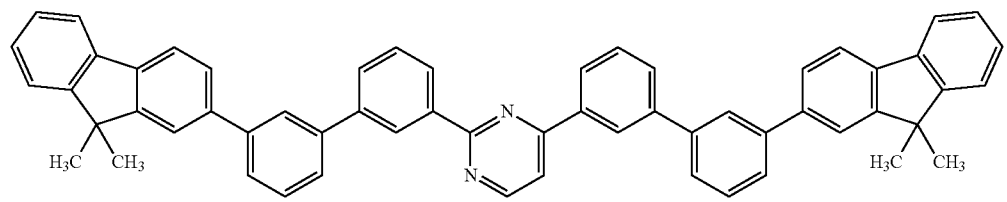
(119)
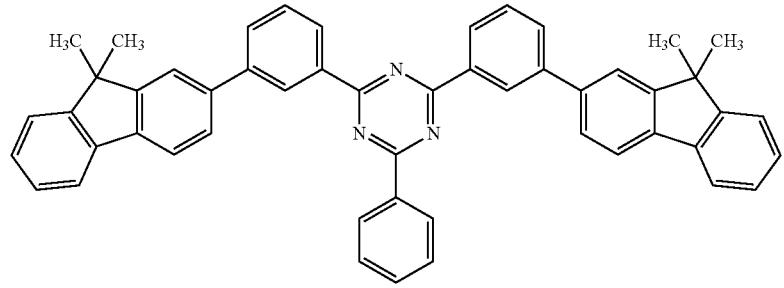
(120)
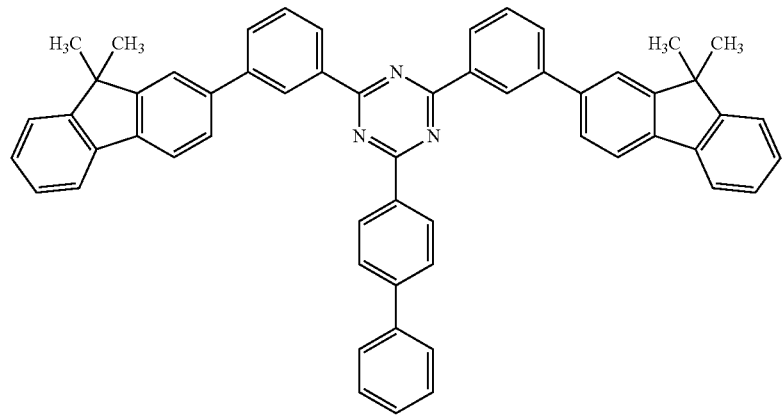
(121)

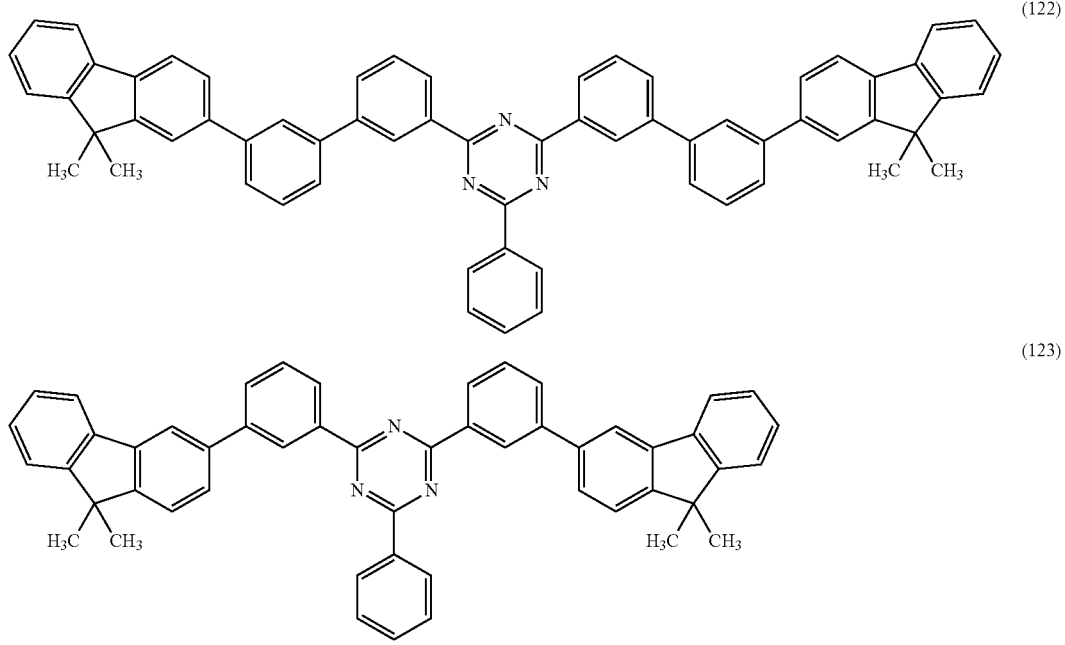

The heterocyclic compound of one embodiment of the present invention has a heterocyclic skeleton (a pyrimidine skeleton or a triazine skeleton) which is an electron-transport skeleton and a fluorene skeleton which is a hole-transport skeleton; therefore, the heterocyclic compound can easily receive an electron and a hole. Accordingly, with the use of the heterocyclic compound of one embodiment of the present invention as a host material of a light-emitting layer, recombination between electrons and holes in a desired region in the light-emitting layer is possible, which inhibits a reduction in lifetime of the light-emitting element.

In the heterocyclic compound of one embodiment of the present invention, a heterocyclic skeleton is bonded to a fluorene skeleton through an arylene group, whereby the extension of a conjugated system can be inhibited and a reduction in band gap and a reduction in triplet excitation energy can be prevented.

Note that the structure described in this embodiment can be combined as appropriate with any of the structures described in the other embodiments.

Embodiment 2

In this embodiment, a light-emitting element in which the heterocyclic compound of one embodiment of the present invention can be used as an EL material is described with reference to FIG. 1.

Figure 1:
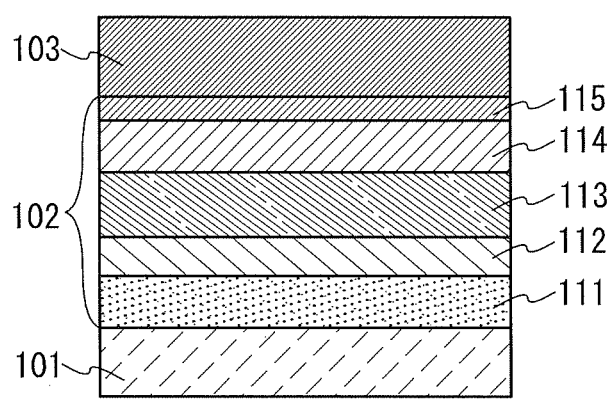
FIG. 1 illustrates a structure of a light-emitting element.

In a light-emitting element described in this embodiment, as illustrated in FIG. 1, an EL layer 102 including a light-emitting layer 113 is interposed between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, and the like in addition to the light-emitting layer 113.

When voltage is applied to such a light-emitting element, holes injected from the first electrode 101 side and electrons injected from the second electrode 103 side recombine in the light-emitting layer 113 to raise a light-emitting substance contained in the light-emitting layer 113 to an excited state. The light-emitting substance in the excited state emits light when it returns to the ground state.

Although the heterocyclic compound of one embodiment of the present invention can be used for any one or more layers in the EL layer 102 described in this embodiment, the heterocyclic compound is preferably used for the light-emitting layer 113, the hole-transport layer 112, or the electron-transport layer 114. In other words, the heterocyclic compound is used in part of a light-emitting element having a structure described below.

A preferred specific example in which the light-emitting element described in this embodiment is fabricated is described below.

As the first electrode (anode) 101 and the second electrode (cathode) 103, a metal, an alloy, an electrically conductive compound, a mixture thereof, and the like can be used. Specific examples are indium oxide-tin oxide (indium tin oxide (ITO)), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg or AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method or an evaporation method (including a vacuum evaporation method).

The hole-injection layer 111 injects holes into the light-emitting layer 113 through the hole-transport layer 112 having a high hole-transport property. The hole-injection layer 111 contains a substance having a high hole-transport property and an acceptor substance, so that electrons are extracted from the substance having a high hole-transport property by the acceptor substance to generate holes and the holes are injected into the light-emitting layer 113 through the hole-transport layer 112. The hole-transport layer 112 is formed using a substance having a high hole-transport property.

Specific examples of the substance having a high hole-transport property, which is used for the hole-injection layer 111 and the hole-transport layer 112, include aromatic amine compounds such as 4,4'-bis[N-(1-naphthyl)-N-phenylamino]biphenyl (abbreviation: NPB or a-NPD), N,N'-bis (3-methylphenyl)-N,N'-diphenyl-[1,1'biphenyl]-4,4'-diamine (abbreviation: TPD), 4,4',4''-tris(carbazol-9-yl) triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA$^1$); 3,6-bis[N-(9-phenylcarbazol-3-yl)-N-phenylamino]-9-phenylcarbazole (abbreviation: PCzPCA$^2$); and 3-[N-(1-naphthyl)-N-(9-phenylcarbazol-3-yl)amino]-9-phenylcarbazole (abbreviation: PCzPCN1). Other examples include carbazole derivatives such as 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances listed here are mainly ones that have a hole mobility of $1 \times 10^{-6}$ cm$^2$Ns or higher. Note that any substance other than the substances listed here may be used as long as the hole-transport property is higher than the electron-transport property.

A high molecular compound such as poly(N-vinylcarbazole) (abbreviation: PVK), poly(4-vinyltriphenylamine) (abbreviation: PVTPA), poly[N-(4-{N'-[4-(4-diphenylamino) phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Examples of the acceptor substance that is used for the hole-injection layer 111 include oxides of metals belonging to Groups 4 to 8 of the periodic table. Specifically, molybdenum oxide is particularly preferable.

The light-emitting layer 113 is a layer containing a light-emitting substance. The light-emitting layer 113 may contain only a light-emitting substance; alternatively, an emission center substance (guest material) may be dispersed in a host material in the light-emitting layer 113. Note that as the host material, the above-described substance having a high hole-transport property or a later-described substance having a high electron-transport property can be used, and preferably, a substance having high triplet excitation energy is used. In addition, the heterocyclic compound described in Embodiment 1, which is one embodiment of the present invention, can be used in combination.

There is no particular limitation on the material that can be used as the light-emitting substance and the emission center substance in the light-emitting layer 113. A light-emitting substance converting singlet excitation energy into luminescence (hereinafter, referred to as fluorescent substance) or a light-emitting substance converting triplet excitation energy into luminescence (hereinafter, referred to as phosphorescent substance) can be used. Examples of the light-emitting substance and the emission center substance are given below.

As an example of the light-emitting substance converting singlet excitation energy into luminescence, a substance emitting fluorescence can be given.

Examples of the substance emitting fluorescence include N,N'-bis[4-(9H-carbazol-9-yl)phenyl]-N,N'-diphenylstilbene-4,4'-diamine (abbreviation: YGA$^2$S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9, 10-diyldi-4,1-phenylene)bis[N,N',N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl) phenyl]-N,N',N'-triphenyl-1,4-phenylenediamine (abbreviation: 2DPAPPA), N,N,N',N',N''N'',N''',N'''-octaphenyldibenzo[g,p]chrysene-2,7,10,15-tetraamine (abbreviation: DBC 1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N'N-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-H,5H-benzo[j]quinolizin-9-yl)ethenyl]-4H-pyran-4-ylidene}propanedinitrile (abbreviation: DCM2), N,N,N',N'-tetrakis(4-methylphenyl) tetracene-5,11-diamine (abbreviation: p-mPhTD), 7,14-diphenyl-N,N,N',N''-tetrakis(4-methylphenyl)acenaphtho[1, 2-a]fluoranthene-3,10-diamine (abbreviation: p-mPhAFD), {2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), {2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2, 6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

Examples of the light-emitting substance converting triplet excitation energy into luminescence include a substance emitting phosphorescence and a thermally activated delayed fluorescence (TADF) material. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the substance emitting phosphorescence include bis{2-[3',5'-bis(trifluoromethyl)phenyl]pyridinato-N,C$^2$}iridium(III) picolinate (abbreviation: Ir(CF$_3$ppy)$_2$ (pic)), bis[2-(4',6'-difluorophenyl)pyridinato-N,C$^{2'}$]iridium (III) acetylacetonate (abbreviation: FIracac), tris(2- phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato) (monophenanthroline)terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,C$^{2'}$)iridium(III) acetylacetonate (abbreviation: Ir(dpo)$_2$(acac)), bis{2-[4'-(perfluorophenyl)phenyl]pyridinato-N,C$^{2'}$}iridium(III) acetylacetonate (abbreviation: Ir(p-PF-ph)$_2$(acac)), bis(2-phenylbenzothiazolato-N,C$^{2'}$)iridium(III) acetylacetonate (abbreviation: Ir(bt)$_2$(acac)), bis[2-(2'-benzo[4,5-a]thienyl)pyridinato-N,C$^{3'}$]iridium(III) acetylacetonate (abbreviation: Ir(btp)$_2$(acac)), bis(1-phenylisoquinolinato-N, C)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$(acac)]), (acetylacetonato)bis(2,3,5-triphenylpyrazinato)iridium(III) (abbreviation: Ir(tppr)$_2$(acac)), bis(2,3,5-triphenylpyrazinato) (dipivaloylmethanato)iridium(III) (abbreviation: [Ir(tppr)$_2$(dpm)], (acetylacetonato)bis(6-tert-butyl-4-phenylpyrimidinato)iridium(III) (abbreviation: [Ir(t-Buppmh(acac)]), (acetylacetonato)bis(4,6-diphenylpyrimidinato)iridium(III) (abbreviation: [Ir(dppm)$_2$(acac)]), 2,3,7,8,12,13,17,18-octaethyl-21H,23H-porphyrin platinum(II) (abbreviation: PtOEP), tris(1,3-diphenyl-1,3-propanedionato) (monophenanthroline)europium(II) (abbreviation: Eu(DBM)$_3$(Phen)), and tris[1-(2-thenoyl)-3,3,3-trifluoroacetonato] (monophenanthroline)europium(III) (abbreviation: Eu(TTA)$_3$(Phen)).

Preferable examples of the substance (i.e., host material) used for dispersing the light-emitting substance converting triplet excitation energy into luminescence include compounds having an arylamine skeleton, such as 2,3-bis(4-diphenylaminophenyl)quinoxaline (abbreviation: TPAQn) and NPB, carbazole derivatives such as CBP and 4,4',4"-tris(carbazol-9-yl)triphenylamine (abbreviation: TCTA), and metal complexes such as bis[2-(2-hydroxyphenyl)pyridinato]zinc (abbreviation: Znpp$_2$), bis[2-(2-hydroxyphenyl)benzoxazolato]zinc (abbreviation: Zn(BOX)$_2$), bis(2-methyl-8-quinolinolatoX4-phenylphenolato)aluminum (abbreviation: BAlq), and tris(8-quinolinolato)aluminum (abbreviation: Alq$_3$). Alternatively, a high molecular compound such as PVK can be used.

Examples of the TADF material includes fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP). Alternatively, a heterocyclic compound including a π-electron rich heteroaromatic ring and a n-electron deficient heteroaromatic ring can be used, such as 2-(biphenyl-4-yl)-4,6-bis(12-phenylindolo[2,3-a]carbazol-11 1-yl)-1,3,5-triazine (PIC-TRZ). Note that a material in which the n-electron rich heteroaromatic ring is directly bonded to the n-electron deficient heteroaromatic ring is particularly preferably used because both the donor property of the n-electron rich heteroaromatic ring and the acceptor property of the I-electron deficient heteroaromatic ring are increased and the energy difference between the S1 level and the T1 level becomes small.

When the light-emitting layer 113 includes one or more kinds of host materials and a light-emitting substance converting singlet excitation energy into luminescence or any of the light-emitting substances converting triplet excitation energy into luminescence (i.e., a guest material), light emission with high emission efficiency can be obtained from the light-emitting layer 113. When two or more kinds of host materials are used, they are preferably a combination which can form an exciplex.

The light-emitting layer 113 may have a stacked structure. In that case, each layer in the stacked structure emits light. For example, fluorescence is obtained from a first light-emitting layer in the stacked structure, and phosphorescence is obtained from a second light-emitting layer stacked over the first layer. Note that the stacking order may be reversed. It is preferable that light emission due to energy transfer from an excited complex to a dopant be obtained from the layer that emits phosphorescence. In the case where blue light emission is obtained from one of the first and second layers, orange or yellow light emission can be obtained from the other layer. Each layer may contain various kinds of dopants.

The electron-transport layer 114 is a layer containing a substance having a high electron-transport property. For the electron-transport layer 114, a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), bis(2-methyl-8-quinolinolatoX4-phenylphenolato)aluminum (abbreviation: BAlq), bis[2-(2-hydroxyphenyl)benzoxazolato]zinc (abbreviation: Zn(BOX)$_2$), or bis[2-(2-hydroxyphenyl)benzothiazolato]zinc (abbreviation: Zn(BTZ)$_2$) can be used. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can also be used. A high molecular compound such as poly(2,5-pyridinediyl)(abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can also be used. The substances listed here are mainly ones that have an electron mobility of $1\times10^{-6}$ cm$^2$/Vs or higher. Note that any substance other than the substances listed here may be used for the electron-transport layer 114 as long as the electron-transport property is higher than the hole-transport property. The heterocyclic compound described in Embodiment 1, which is one embodiment of the present invention, can also be used.

The electron-transport layer 114 is not limited to a single layer, but may be a stack of two or more layers each containing any of the substances listed above.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. An electride may also be used for the electron-injection layer 115. Examples of the electride include a substance in which electrons are added at high concentration to calcium oxide-aluminum oxide. Any of the substances for forming the electron-transport layer 114, which are given above, can be used.

A composite material in which an organic compound and an electron donor (donor) are mixed may also be used for the electron-injection layer 115. Such a composite material is excellent in an electron-injection property and an electron-transport property because electrons are generated in the organic compound by the electron donor. In this case, the organic compound is preferably a material that is excellent in transporting the generated electrons. Specifically, for example, the substances for forming the electron-transport layer 114 (e.g., a metal complex or a heteroaromatic compound), which are given above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, and ytterbium are given. In addition, an alkali metal oxide or an alkaline earth metal oxide is preferable, and lithium oxide, calcium oxide, and barium oxide are given. A Lewis base such as magnesium oxide can also be used. An organic compound such as tetrathiafulvalene (abbreviation: TTF) can also be used.

Note that each of the above-described hole-injection layer 111, hole-transport layer 112, light-emitting layer 113, electron-transport layer 114, and electron-injection layer 115 can be formed by a method such as an evaporation method (e.g., a vacuum evaporation method), an ink-jet method, or a coating method.

In the above-described light-emitting element, holes and electrons are recombined in the EL layer 102, whereby light is emitted. Then, the emitted light is extracted outside through one or both of the first electrode 101 and the second electrode 103. Thus, one or both of the first electrode 101 and the second electrode 103 are electrodes having light-transmitting properties.

The light-emitting element described in this embodiment is an example of a light-emitting element in which the heterocyclic compound of one embodiment of the present invention is used as an EL material. Note that the heterocyclic compound of one embodiment of the present invention has high solubility and is easy to purify by sublimation in synthesis; therefore it can be highly purified. Accordingly, by using the heterocyclic compound which is one embodiment of the present invention, a highly reliable light-emitting element can be obtained.

Note that the structure described in this embodiment can be combined as appropriate with any of the structures described in the other embodiments.

Embodiment 3

Described in this embodiment is a light-emitting element (hereinafter, a tandem light-emitting element) which has a structure in which a charge-generation layer is provided between a plurality of EL layers and the heterocyclic compound which is one embodiment of the present invention is used as an EL material in the EL layers.

Figure 2A:
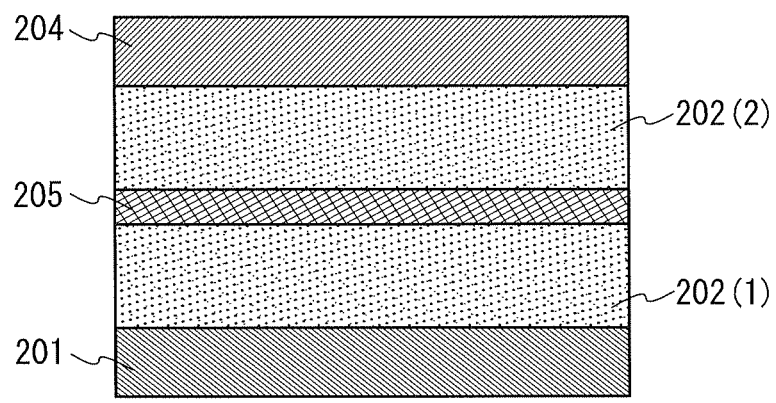
FIGS. 2A and 2B illustrate a structure of a light-emitting element.

A light-emitting element described in this embodiment is a tandem light-emitting element including a plurality of EL layers (a first EL layer 202(1) and a second EL layer 202(2)) between a pair of electrodes (a first electrode 201 and a second electrode 204), as illustrated in FIG. 2A.

In this embodiment, the first electrode 201 functions as an anode, and the second electrode 204 functions as a cathode. Note that the first electrode 201 and the second electrode 204 can have structures similar to those described in Embodiment 2. In addition, either or both of the EL layers (the first EL layer 202(1) and the second EL layer 202(2)) may have structures similar to those described in Embodiment 2. In other words, the structures of the first EL layer 202(1) and the second EL layer 202(2) may be the same or different from each other and can be similar to those of the EL layers described in Embodiment 2.

In addition, a charge-generation layer 205 is provided between the plurality of EL layers (the first EL layer 202(1) and the second EL layer 202(2)). The charge-generation layer 205 has a function of injecting electrons into one of the EL layers and injecting holes into the other of the EL layers when voltage is applied between the first electrode 201 and the second electrode 204. In this embodiment, when voltage is applied such that the potential of the first electrode 201 is higher than that of the second electrode 204, the charge-generation layer 205 injects electrons into the first EL layer 202(1) and injects holes into the second EL layer 202(2).

Note that in terms of light extraction efficiency, the charge-generation layer 205 preferably has a property of transmitting visible light (specifically, the charge-generation layer (I) 205 has a visible light transmittance of 40% or more). The charge-generation layer 205 functions even when it has lower conductivity than the first electrode 201 or the second electrode 204.

The charge-generation layer 205 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or BSPB, or the like can be used. The substances listed here are mainly ones that have a hole mobility of $1 \times 10^{-6}$ cm$^2$N/Vs or higher. Note that any organic compound other than the compounds listed here may be used as long as the hole-transport property is higher than the electron-transport property.

As the electron acceptor, 7,7,8,8-tetracyano-2,3,5,6-tetrafluoroquinodimethane (abbreviation: F$_4$-TCNQ), chloranil, and the like can be given. Oxides of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easy to handle.

In the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as $Zn(BOX)_2$ or $Zn(BTZ)_2$ can be used. Alternatively, in addition to such a metal complex, PBD, OXD-7, TAZ, Bphen, BCP, or the like can be used. The substances listed here are mainly ones that have an electron mobility of $1\times10^{-6}$ cm²Ns or higher. Note that any organic compound other than the compounds listed here may be used as long as the electron-transport property is higher than the hole-transport property.

As the electron donor, it is possible to use an alkali metal, an alkaline earth metal, a rare earth metal, metals belonging to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that forming the charge-generation layer 205 by using any of the above materials can suppress a drive voltage increase caused by the stack of the EL layers.

Figure 2B:
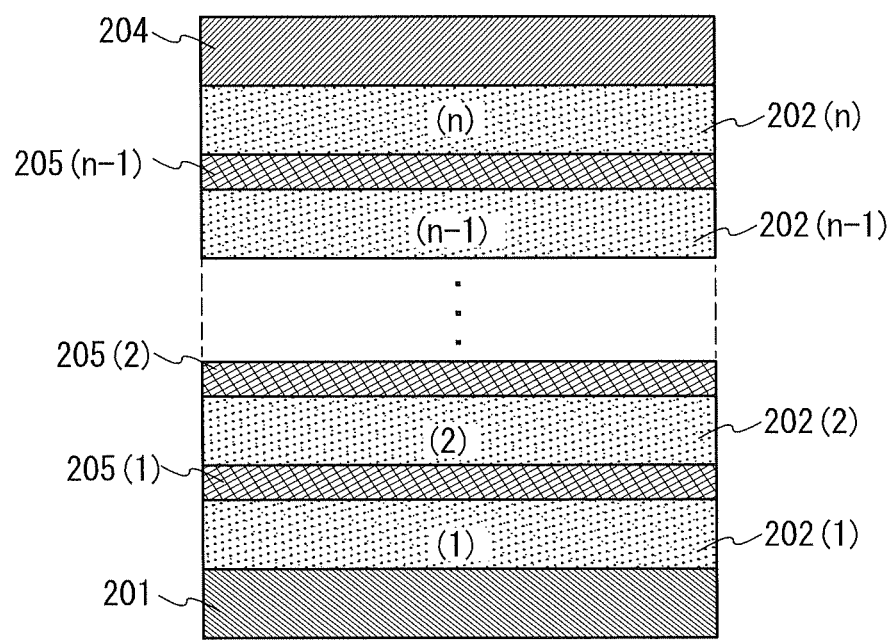

Although the light-emitting element including two EL layers is described in this embodiment, the present invention can be similarly applied to a light-emitting element in which n EL layers (202(1) to 202(n)) (n is three or more) are stacked as illustrated in FIG. 2B. In the case where a plurality of EL layers are included between a pair of electrodes as in the light-emitting element according to this embodiment, by providing charge-generation layers (205(1) to 205(n−1)) between the EL layers, light emission in a high luminance region can be obtained with current density kept low. Since the current density can be kept low, the element can have a long lifetime. When the light-emitting element is applied to light-emitting devices, electronic appliances, and lighting devices each having a large light-emitting area, voltage drop due to resistance of an electrode material can be reduced, which results in uniform light emission in a large area.

When the EL layers have different emission colors, a desired emission color can be obtained from the whole light-emitting element. For example, in a light-emitting element having two EL layers, when an emission color of the first EL layer and an emission color of the second EL layer are complementary colors, the light-emitting element can emit white light as a whole. Note that "complementary colors" refer to colors that can produce an achromatic color when mixed. In other words, emission of white light can be obtained by mixture of light emitted from substances whose emission colors are complementary colors. Specifically, a combination in which blue light emission is obtained from the first EL layer and yellow light emission or orange light emission is obtained from the second EL layer is given as an example. In that case, it is not necessary that both of blue light emission and yellow (or orange) light emission are fluorescence, and the both are not necessarily phosphorescence. For example, a combination in which blue light emission is fluorescence and yellow (or orange) light emission is phosphorescence or a combination in which blue light emission is phosphorescence and yellow (or orange) light emission is fluorescence may be employed.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 4

Described in this embodiment is a light-emitting device that includes a light-emitting element in which the heterocyclic compound which is one embodiment of the present invention is used for an EL layer.

The light-emitting device may be either a passive matrix type light-emitting device or an active matrix type light-emitting device. Note that any of the light-emitting elements described in the other embodiments can be used for the light-emitting device described in this embodiment.

In this embodiment, an active matrix light-emitting device is described with reference to FIGS. 3A and 3B.

Note that FIG. 3A is a top view illustrating a light-emitting device and FIG. 3B is a cross-sectional view taken along the chain line A-A' in FIG. 3A. The active matrix light-emitting device according to this embodiment includes a pixel portion 302 provided over an element substrate 301, a driver circuit portion (a source line driver circuit) 303, and driver circuit portions 304a and 304b. The pixel portion 302, the driver circuit portion 303, and the driver circuit portions 304a and 304b are sealed between the element substrate 301 and a sealing substrate 306 with a sealant 305.

In addition, over the element substrate 301, a lead wiring 307 for connecting an external input terminal, through which a signal (e.g., a video signal, a clock signal, a start signal, a reset signal, or the like) or electric potential from the outside is transmitted to the driver circuit portion 303 and the driver circuit portions 304a and 304b, is provided. Here, an example is described in which a flexible printed circuit (FPC) 308 is provided as the external input terminal. Although only the FPC is illustrated here, the FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 3B. The driver circuit portion and the pixel portion are formed over the element substrate 301; the driver circuit portion 303 that is the source line driver circuit and the pixel portion 302 are illustrated here.

The driver circuit portion 303 is an example in which an FET 309 and an FET 310 are combined. Note that the driver circuit portion 303 may be formed with a circuit including transistors having the same conductivity type (either n-channel transistors or p-channel transistors) or a CMOS circuit including an n-channel transistor and a p-channel transistor. Although this embodiment shows a driver integrated type in which the driver circuit is formed over the substrate, the driver circuit is not necessarily formed over the substrate, and may be formed outside the substrate.

The pixel portion 302 includes a plurality of pixels each of which includes a switching FET 311, a current control FET 312, and a first electrode (anode) 313 which is electrically connected to a wiring (a source electrode or a drain electrode) of the current control FET 312. Although the pixel portion 302 includes two FETs, the switching FET 311 and the current control FET 312, in this embodiment, one embodiment of the present invention is not limited thereto. The pixel portion 302 may include, for example, three or more FETs and a capacitor in combination.

As the FETs 309, 310, 311, and 312, for example, a staggered transistor or an inverted staggered transistor can be used. For example, a Group 13 semiconductor (e.g., gallium), a Group 14 semiconductor (e.g., silicon), a compound semiconductor, an oxide semiconductor, or an organic semiconductor can be used. In addition, there is no particular limitation on the crystallinity of the semiconductor material, and an amorphous semiconductor or a crystalline semiconductor can be used. In particular, an oxide semiconductor is preferably used for the FETs 309, 310, 311, and 312. Examples of the oxide semiconductor include an In—Ga oxide and an In-M-Zn oxide (M is Al, Ga, Y, Zr, La, Ce, or Nd). For example, an oxide semiconductor that has an energy gap of 2 eV or more, preferably 2.5 eV or more, further preferably 3 eV or more is used for the FETs 309, 310, 311, and 312, so that the off-state current of the transistors can be reduced.

In addition, an insulator 314 is formed to cover end portions of the first electrode (anode) 313. In this embodiment, the insulator 314 is formed using a positive photosensitive acrylic resin. The first electrode 313 is used as an anode in this embodiment.

The insulator 314 preferably has a curved surface with curvature at an upper end portion or a lower end portion thereof. This enables the coverage with a film to be formed over the insulator 314 to be favorable. The insulator 314 can be formed using, for example, either a negative photosensitive resin or a positive photosensitive resin. The material of the insulator 314 is not limited to an organic compound and an inorganic compound such as silicon oxide, silicon oxynitride, or silicon nitride can also be used.

An EL layer 315 and a second electrode (cathode) 316 are stacked over the first electrode (anode) 313. In the EL layer 315, at least a light-emitting layer is provided. In the EL layer 315, a hole-injection layer, a hole-transport layer, an electron-transport layer, an electron-injection layer, a charge-generation layer, and the like can be provided as appropriate in addition to the light-emitting layer.

A light-emitting element 317 is formed of a stack of the first electrode (anode) 313, the EL layer 315, and the second electrode (cathode) 316. For the first electrode (anode) 313, the EL layer 315, and the second electrode (cathode) 316, any of the materials given in Embodiment 2 can be used. Although not illustrated, the second electrode (cathode) 316 is electrically connected to the FPC 308 which is an external input terminal.

Although the cross-sectional view in FIG. 3B illustrates only one light-emitting element 317, a plurality of light-emitting elements are arranged in a matrix in the pixel portion 302. Light-emitting elements that emit light of three kinds of colors (R, G, and B) are selectively formed in the pixel portion 302, whereby a light-emitting device capable of full color display can be obtained. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of a plurality of kinds of colors are used in combination with the light-emitting elements that emit light of three kinds of colors (R, G, and B), whereby effects such as an improvement in color purity and a reduction in power consumption can be obtained. Alternatively, the light-emitting device may be capable of full color display by combination with color filters. The light-emitting device may have improved emission efficiency and reduced power consumption by combination with quantum dots.

Furthermore, the sealing substrate 306 is attached to the element substrate 301 with the sealant 305, whereby a light-emitting element 317 is provided in a space 318 surrounded by the element substrate 301, the sealing substrate 306, and the sealant 305. Note that the space 318 may be filled with an inert gas (such as nitrogen and argon) or the sealant 305.

An epoxy-based resin or glass frit is preferably used for the sealant 305. The material preferably allows as little moisture and oxygen as possible to penetrate. As the sealing substrate 306, a glass substrate, a quartz substrate, or a plastic substrate formed of fiber-reinforced plastic (FRP), poly(vinyl fluoride) (PVF), polyester, an acrylic resin, or the like can be used. In the case where glass frit is used as the sealant, the element substrate 301 and the sealing substrate 306 are preferably glass substrates for high adhesion.

As described above, an active matrix light-emitting device can be obtained.

Note that the structure described in this embodiment can be combined as appropriate with any of the structures described in the other embodiments.

Embodiment 5

In this embodiment, examples of an electronic appliance manufactured using a light-emitting device which is one embodiment of the present invention are described with reference to FIGS. 4A to 4D'2 and FIGS. 5A to 5C.

Examples of the electronic appliance including the light-emitting device are television devices (also referred to as TV or television receivers), monitors for computers and the like, cameras such as digital cameras and digital video cameras, digital photo frames, cellular phones (also referred to as portable telephone devices), portable game consoles, portable information terminals, audio playback devices, large game machines such as pachinko machines, and the like. Specific examples of the electronic appliances are illustrated in FIGS. 4A to 4D.

Figure 4A:
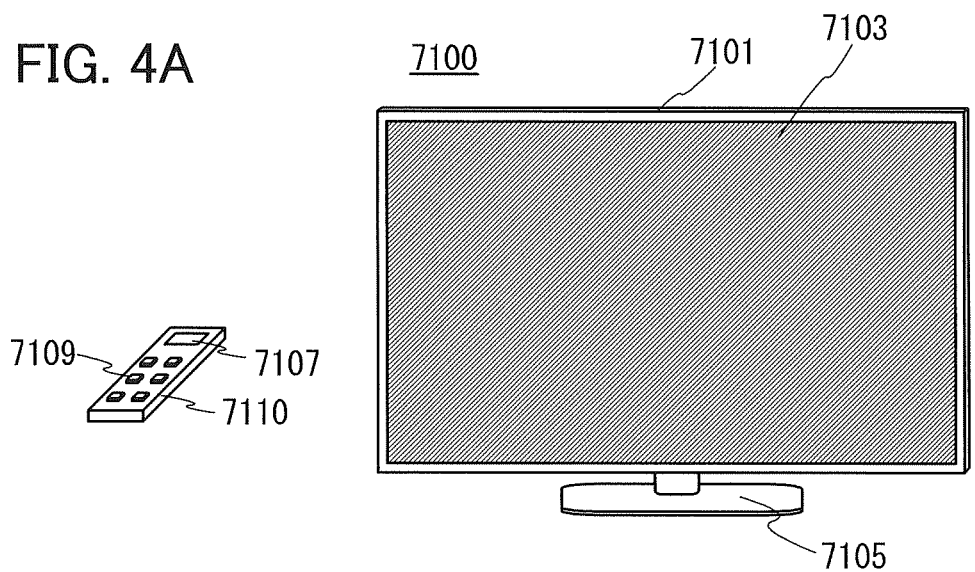

FIG. 4A illustrates an example of a television device. In the television device 7100, a display portion 7103 is incorporated in a housing 7101. The display portion 7103 can display images and may be a touch panel (an input/output device) including a touch sensor (an input device). Note that the light-emitting device which is one embodiment of the present invention can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the use of the receiver, general television broadcasts can be received. Moreover, when the television device is connected to a communication network with or without wires via the modem, one-way (from a sender to a receiver) or two-way (between a sender and a receiver or between receivers) information communication can be performed.

Figure 4B:
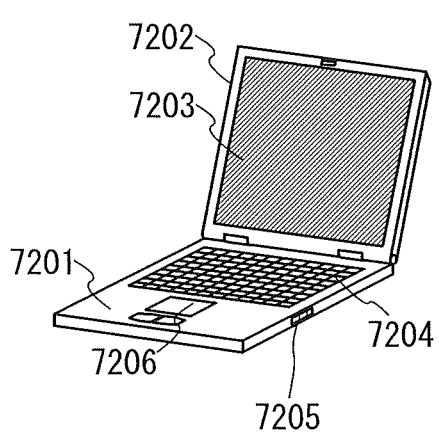

FIG. 4B illustrates a computer, which includes a main body 7201, a housing 7202, a display portion 7203, a keyboard 7204, an external connection port 7205, a pointing device 7206, and the like. Note that this computer can be manufactured using the light-emitting device which is one embodiment of the present invention for the display portion

7203. The display portion 7203 may be a touch panel (an input/output device) including a touch sensor (an input device).

Figure 4C:
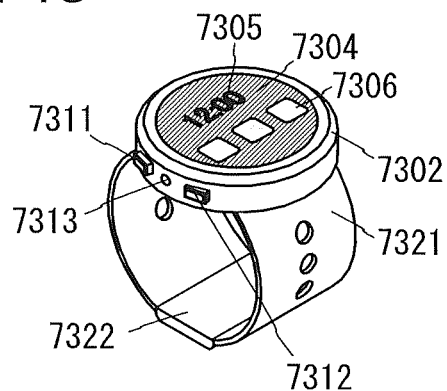

FIG. 4C illustrates a smart watch, which includes a housing 7302, a display panel 7304, operation buttons 7311 and 7312, a connection terminal 7313, a band 7321, a clasp 7322, and the like.

The display panel 7304 mounted in the housing 7302 serving as a bezel includes a non-rectangular display region. The display panel 7304 can display an icon 7305 indicating time, another icon 7306, and the like. The display panel 7304 may be a touch panel (an input/output device) including a touch sensor (an input device).

The smart watch illustrated in FIG. 4C can have a variety of functions, for example, a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading program or data stored in a recording medium and displaying the program or data on a display portion.

The housing 7302 can include a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like. Note that the smart watch can be manufactured using the light-emitting device for the display panel 7304.

Figure 4D:
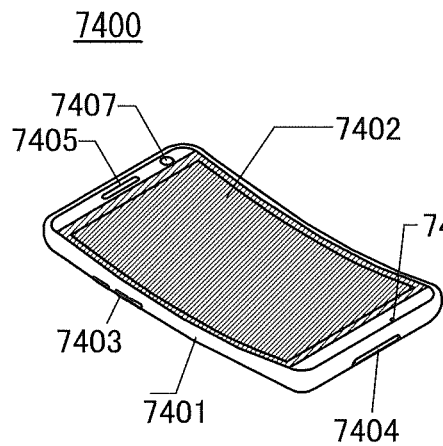
Figure 4D:
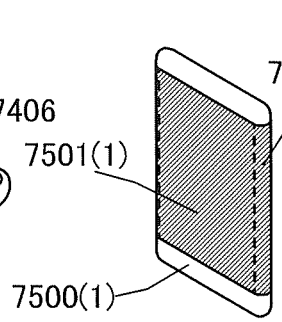
Figure 4D:
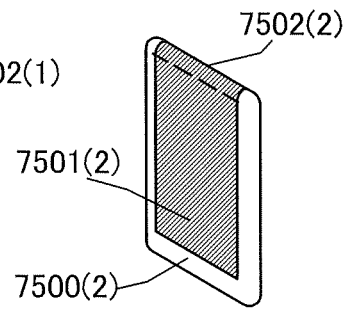

FIG. 4D illustrates an example of a cellular phone (e.g., smartphone). A cellular phone 7400 includes a housing 7401 provided with a display portion 7402, a microphone 7406, a speaker 7405, a camera 7407, an external connection portion 7404, an operation button 7403, and the like. In the case where a light-emitting device is manufactured by forming a light-emitting element of one embodiment of the present invention over a flexible substrate, the light-emitting element can be used for the display portion 7402 having a curved surface as illustrated in FIG. 4D.

When the display portion 7402 of the cellular phone 7400 illustrated in FIG. 4D is touched with a finger or the like, data can be input to the cellular phone 7400. In addition, operations such as making a call and composing an e-mail can be performed by touch on the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device such as a gyroscope or an acceleration sensor is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal authentication can be performed. In addition, by providing a backlight or a sensing light source that emits near-infrared light in the display portion, an image of a finger vein, a palm vein, or the like can be taken.

The light-emitting device can be used for a cellular phone having a structure illustrated in FIG. 4D'1 or FIG. 4D'2, which is another structure of the cellular phone (e.g., smartphone).

Note that in the case of the structure illustrated in FIG. 4D'1 or FIG. 4D'2, text data, image data, or the like can be displayed on second screens 7502(1) and 7502(2) of housings 7500(1) and 7500(2) as well as first screens 7501(1) and 7501(2). Such a structure enables a user to easily see text data, image data, or the like displayed on the second screens 7502(1) and 7502(2) while the cellular phone is placed in user's breast pocket.

FIGS. 5A to 5C illustrate a foldable portable information terminal 9310. FIG. 5A illustrates the portable information terminal 9310 which is opened. FIG. 5B illustrates the portable information terminal 9310 which is being opened or being folded. FIG. 5C illustrates the portable information terminal 9310 that is folded. The portable information terminal 9310 is highly portable when folded. When the portable information terminal 9310 is opened, a seamless large display region is highly browsable.

A display panel 9311 is supported by three housings 9315 joined together by hinges 9313. Note that the display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. A light-emitting device of one embodiment of the present invention can be used for the display panel 9311. A display region 9312 is a display region that positioned at a side surface of the portable information terminal 9310 that is folded. On the display region 9312, information icons, file shortcuts of frequently used applications or programs, and the like can be displayed, and confirmation of information and start of application can be smoothly performed.

As described above, the electronic appliances can be obtained using the light-emitting device which is one embodiment of the present invention. Note that the light-emitting device can be used for electronic appliances in a variety of fields without being limited to the electronic appliances described in this embodiment.

Note that the structure described in this embodiment can be combined as appropriate with any of the structures described in the other embodiments.

Embodiment 6

In this embodiment, examples of a lighting device including the light-emitting device of one embodiment of the present invention are described with reference to FIG. 6.

FIG. 6 illustrates an example in which the light-emitting device is used as an indoor lighting device 8001. Since the light-emitting device can have a large area, it can be used for a lighting device having a large area. In addition, with the use of a housing with a curved surface, a lighting device 8002 which includes the housing, a cover, or a support and in which a light-emitting region has a curved surface can also be obtained. A light-emitting element included in the light-emitting device described in this embodiment is in a thin film form, which allows the housing to be designed more freely. Thus, the lighting device can be elaborately designed in a variety of ways. In addition, a wall of the room may be provided with a large-sized lighting device 8003.

When the light-emitting device is used for a table by being used as a surface of a table, a lighting device 8004 that has a function as a table can be obtained. When the light-emitting device is used as part of other furniture, a lighting device that functions as the furniture can be obtained.

As described above, a variety of lighting devices that include the light-emitting device can be obtained. Note that these lighting devices are also embodiments of the present invention.

Note that the structure described in this embodiment can be combined as appropriate with any of the structures described in the other embodiments.

Example 1

Synthesis Example

In this example, a method of synthesizing 4,6-bis[3-(9,9-dimethylfluoren-2-yl)phenyl]pyrimidine (abbreviation: 4,6mFP2Pm) (Structural Formula (100)), which is the heterocyclic compound of one embodiment of the present invention, is described. The structure of 4,6mFP2Pm is shown below.

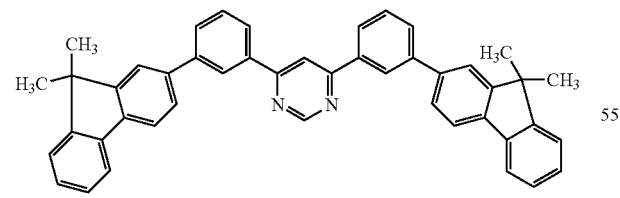

(100)

Step 1: Synthesis of
2-(3-bromophenyl)-9,9-dimethylfluorene

First, 7.8 g (24 mmol) of 9,9-dimethylfluorene-2-boronic acid pinacol ester, 6.2 g (22 mmol) of 3-bromoiodobenzene, 5.0 g (47 mmol) of sodium carbonate, 100 mL of toluene, and 10 mL of ethanol were put in a 300-mL three-neck flask, and the atmosphere in the flask was replaced with nitrogen. To this mixture, 0.42 g (0.36 mmol) of tetrakis(triphenylphosphine)palladium(0) (abbreviation: Pd(PPh$_3$)$_4$) was added and the mixture was heated and stirred at 80° C. for 10 hours. Water was added to the obtained mixture; thus, a mixed solution in which an aqueous layer and an organic layer were separated was obtained. The aqueous layer was extracted with toluene.

The obtained solution of the extract and the organic layer were combined and washed with saturated saline. Anhydrous magnesium sulfate was added to the organic layer for drying, and the resulting mixture was subjected to gravity filtration to give a filtrate. This filtrate was concentrated to give an oily substance. This oily substance was purified by flash column chromatography. As a developing solvent, a mixed solvent of hexane and toluene in a ratio of 3:2 (v/v) was used. The obtained fraction was concentrated to give an oily substance. Hexane was added to this oily substance and the mixture was irradiated with ultrasonic waves, whereby a solid was precipitated. This solid was suction-filtered and then washed with toluene and hexane, whereby 4.8 g of 2-(3-bromophenyl)-9,9-dimethylfluorene (white solid) was obtained in a yield of 57%.

Synthesis scheme (A-1) of Step 1 is shown below.

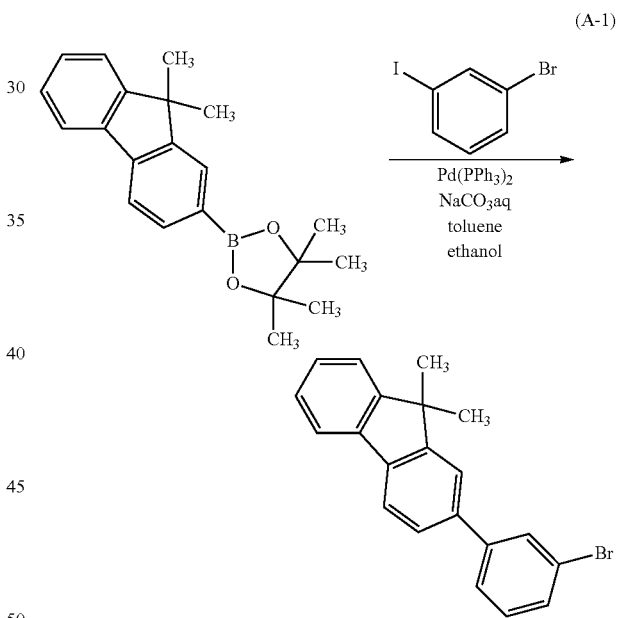

(A-1)

Step 2: Synthesis of
3-(9,9-dimethylfluoren-2-yl)phenylboronic Acid

In a 300-mL three-neck flask was put 4.8 g (14 mmol) of 2-(3-bromophenyl)-9,9-dimethylfluorene. The atmosphere in the flask was replaced with nitrogen. Then, 70 mL of tetrahydrofuran (THF) was added and the mixture was stirred at −78° C. To this mixed solution, 10 mL (15 mmol) of n-butyllithium (a 1.58 mol/L hexane solution) was dropped, and stirring was performed at −78° C. for 1.5 hours. To this mixed solution, 1.8 mL (16 mmol) of trimethyl borate was dropped, and stirring was performed for 18 hours while the temperature was raised to 20° C. After a predetermined time, 100 mL of hydrochloric acid (1 mol/L) was added to the mixed solution, and stirring was performed at room temperature. Thus, the mixed solution was separated into an aqueous layer and an organic layer.

The aqueous layer of the mixed solution was extracted with ethyl acetate, and the solution of the extract and the organic layer were combined and washed with water and saturated saline. Anhydrous magnesium sulfate was added to the organic layer for drying, and the resulting mixture was subjected to gravity filtration to give a filtrate. This filtrate was concentrated to give an oily substance, and hexane was added to this oily substance, whereby a solid was precipitated. This mixture was suction-filtered to give a solid. This solid was washed with a small amount of toluene, whereby 1.9 g of 3-(9,9-dimethylfluoren-2-yl)phenylboronic acid (white solid) was obtained in a yield of 45%.

Synthesis scheme (A-2) of Step 2 is shown below.

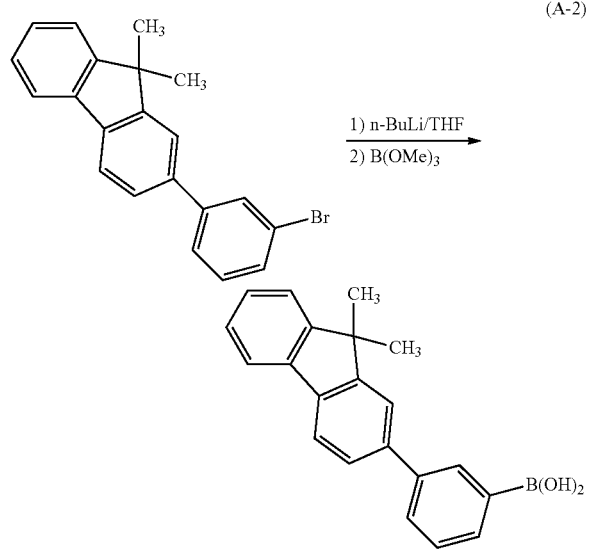

Step 3: Synthesis of 4,6-bis[3-(9,9-dimethylfluoren-2-yl)phenyl]pyrimidine (Abbreviation: 4,6mFP2Pm)

In a 100-mL round-bottom flask were put 1.9 g (6.1 mmol) of 3-(9,9-dimethylfluoren-2-yl)phenylboronic acid, 0.36 g (2.4 mmol) of 4,6-dichloropyrimidine, 1.3 g (12 mmol) of sodium carbonate, 25 mL of 1,3-dimethyl-3,4,5,6-tetrahydro-2(1H)pyrimidinone (DMPU), and 15 mL of water. The atmosphere in the flask was replaced with argon. To this mixture was added 17 mg (0.020 mmol) of bis(triphenylphosphine)palladium(II) dichloride. This mixture was irradiated with microwaves under conditions of 100 W and 150° C. for 1 hour to be reacted.

Water was added to the obtained reaction solution; thus, a mixed solution in which an aqueous layer and an organic layer were separated was obtained. The aqueous layer was extracted with toluene. The obtained solution of the extract was washed with water and saturated saline, and anhydrous magnesium sulfate was added to the organic layer for drying. The resulting mixture was subjected to gravity filtration to give a filtrate. This filtrate was concentrated to give an oily substance. This oily substance was dissolved in toluene, and the resulting solution was suction-filtered through Celite, alumina, and Florisil stacked in this order on a piece of filter paper. The obtained filtrate was concentrated to give a solid. This solid was recrystallized with toluene, whereby 0.9 g of 4,6mFP2Pm (white solid) was obtained in a yield of 61%.

Synthesis scheme (A-3) of Step 3 is shown below.

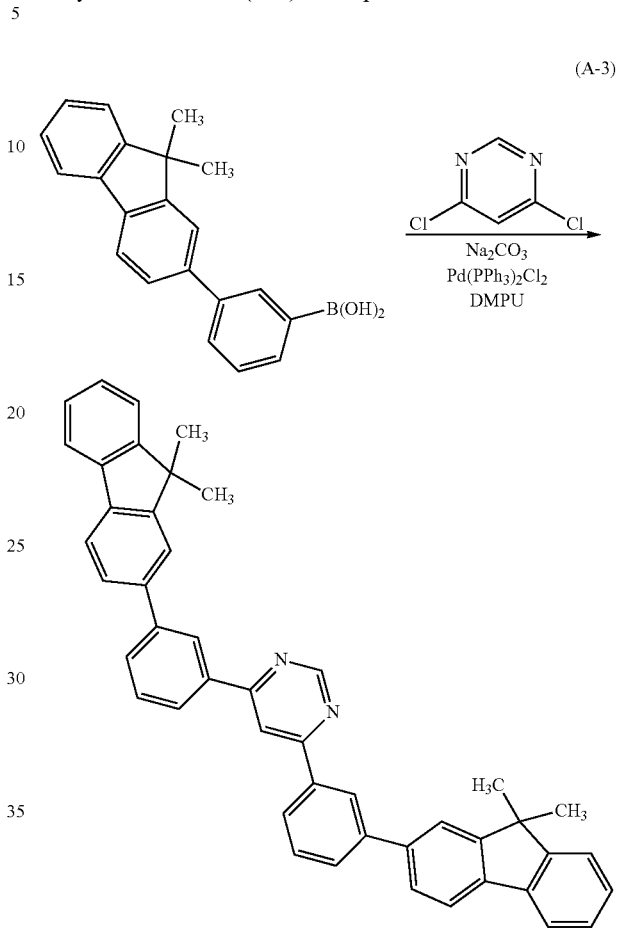

The obtained solid was purified by a train sublimation method. Conditions for the purification by sublimation were set as follows: the pressure was 2.6 Pa, the flow rate of argon gas was 5 mL/min, and the heating temperature was 260° C. After the purification by sublimation, a white solid which was a target substance was obtained at a collection rate of 46%.

The results of analysis by nuclear magnetic resonance ($^1$H-NMR chart) spectroscopy of the white solid obtained in Step 3 are described below. FIG. 7 is a $^1$H-NMR chart. According to the result, 4,6mFP2Pm (Structural Formula (100)), which is the heterocyclic compound of one embodiment of the present invention, was obtained in Step 3.

$^1$H NMR (CDCl$_3$, 500 MHz): δ (ppm)=1.57 (s, 12H), 7.33-7.39 (m, 4H), 7.46-7.48 (m, 2H), 7.64-7.69 (m, 4H), 7.74 (s, 2H), 7.77 (d, 2H), 7.82-7.85 (m, 4H), 8.13 (d, 2H), 8.25 (d, 1H), 8.45 (s, 2H).

Furthermore, 4,6mFP2Pm was analyzed by liquid chromatography mass spectrometry (abbreviation: LC/MS).

The analysis by LC/MS was carried out with Acquity UPLC (manufactured by Waters Corporation), and Xevo G2 Tof MS (manufactured by Waters Corporation).

In the MS, ionization was carried out by an electrospray ionization (abbreviation: ESI) method. At this time, the capillary voltage and the sample cone voltage were set to 3.0 kV and 30 V, respectively, and detection was performed in a positive mode. A component which underwent the ionization under the above-described conditions was collided with an argon gas in a collision cell to dissociate into product ions. The energy (collision energy) for the collision with argon was 70 eV. A mass range for the measurement was m/z=100 to 1200.

FIG. 8 shows the measurement result. According to the result in FIG. 8, product ions of 4,6mFP2Pm, which is the heterocyclic compound of one embodiment of the present invention represented by Structural Formula (100), were detected mainly around m/z=617, m/z=601, m/z=585, and m/z=572. Note that the result in FIG. 8 shows characteristics derived from 4,6mFP2Pm and therefore it can be said that the result is important data for identifying 4,6mFP2Pm contained in the mixture.

Note that a peak around m/z=601 is presumed to be derived from cations in the state where a methyl group and a proton are dissociated from the compound represented by Structural Formula (100). A peak around m/z=585 is presumed to be derived from cations in the state where two methyl groups and a proton are dissociated. A peak around m/z=572 is presumed to be derived from cations in the state where three methyl groups and a proton are dissociated. This indicates that 4,6mFP2Pm, which is the heterocyclic compound of one embodiment of the present invention, contains a plurality of methyl groups.

Example 2

Synthesis Example

In this example, a method of synthesizing 4,6-bis {3-[3-(9,9-dimethylfluoren-2-yl)phenyl]phenyl}pyrimidine (abbreviation: 4,6mFBP2Pm) (Structural Formula (109)), which is the heterocyclic compound of one embodiment of the present invention, is described. The structure of 4,6mFBP2Pm is shown below.

to give an oily substance. This solid was recrystallized with ethanol, whereby 118 g of a brown solid was obtained in a yield of 81%.

Synthesis scheme (B-1) of Step 1 is shown below.

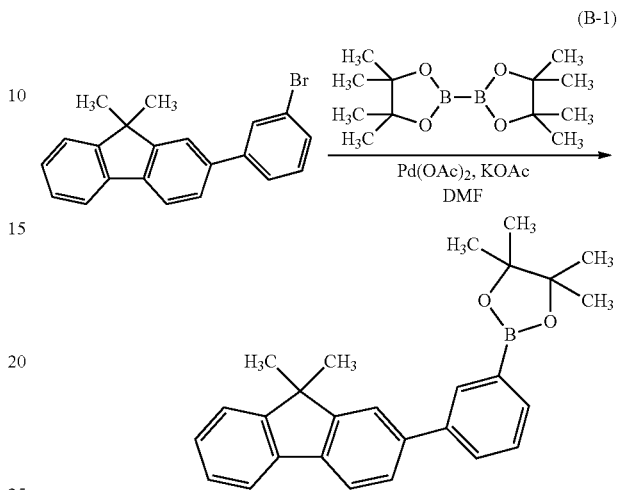

Step 2: Synthesis of 4,6-bis{3-[3-(9,9-dimethylfluoren-2-yl)phenyl]phenyl}pyrimidine (Abbreviation: 4,6mFBP2Pm)

In a 100-mL three-neck flask were put 1.0 g (3.3 mmol) of 4,6-bis(3-chlorophenyl)pyrimidine, 2.9 g (7.3 mmol) of 2-[3-(4,4,5,5-tetramethyl-1,3,2-dioxaborolan-2-yl)phenyl]-9,9-dimethylfluorene, 0.70 g (9.9 mmol) of t-butanol, 5.6 g (11 mmol) of tripotassium phosphate, and 22 mL of 1,4-dioxane. This mixture was degassed by being stirred under

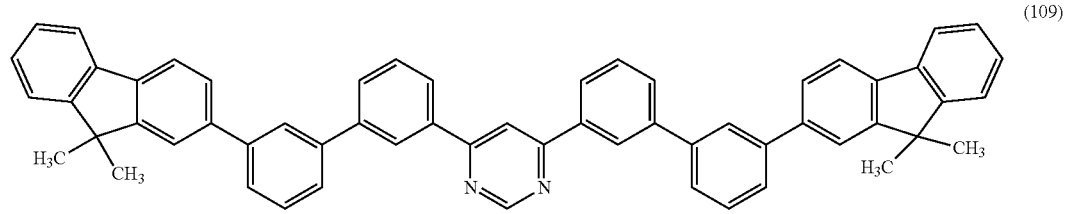 [SMILES: CC1(C)c2ccccc2-c2ccc(-c3cccc(-c4cccc(-c5cc(-c6cccc(-c7cccc(-c8ccc9c(c8)C(C)(C)c8ccccc8-9)c7)c6)ncn5)c4)c3)cc21]

Step 1: Synthesis of 2-[3-(4,4,5,5-tetramethyl-1,3,2-dioxaborolan-2-yl)phenyl]-9,9-dimethylfluorene In a 3-L three-neck flask were put 130 g (0.37 mol) of 2-(3-bromophenyl)-9,9-dimethylfluorene, 103 g (0.41 mol) of 4,4,4',4',5,5,5',5'-octamethyl-2,2'-bi-1,3,2-dioxaborolane, 109 g (1.1 mol) of potassium acetate, and 1.2 L of N,N-dimethylformamide (DMF). This mixture was degassed by being stirred under reduced pressure, and the atmosphere in the flask was replaced with nitrogen. To the mixture was added 2.5 g (0.011 mmol) of palladium(II) acetate, and the mixture was stirred under a nitrogen stream at 100° C. for 5 hours. After a predetermined time, this mixture was suction-filtered through Celite and alumina stacked in this order on a piece of filter paper. The obtained filtrate was concentrated reduced pressure, and the atmosphere in the flask was replaced with nitrogen. To this mixture was added 22 mg (1.0 mmol) of palladium(II) acetate and 71 g (2.0 mmol) of di(1-adamantyl)-n-butylphosphine (another name: cataCXium (registered trademark) A, manufactured by Aldrich) (abbreviation: cataCXium).

This mixture was stirred under a nitrogen stream at 100° C. for 8 hours. After a predetermined time, this mixture was suction-filtered through Celite, and the obtained filtrate was concentrated to give a solid. This solid was purified by silica gel column chromatography. As a developing solvent, a mixed solvent of toluene and hexane in a ratio of 1:1 was used. The obtained fraction was concentrated and dried, and recrystallized with acetonitrile, whereby 3.7 g of a white solid was obtained in a yield of 74%.

Synthesis scheme (β-2) of Step 2 is shown below.

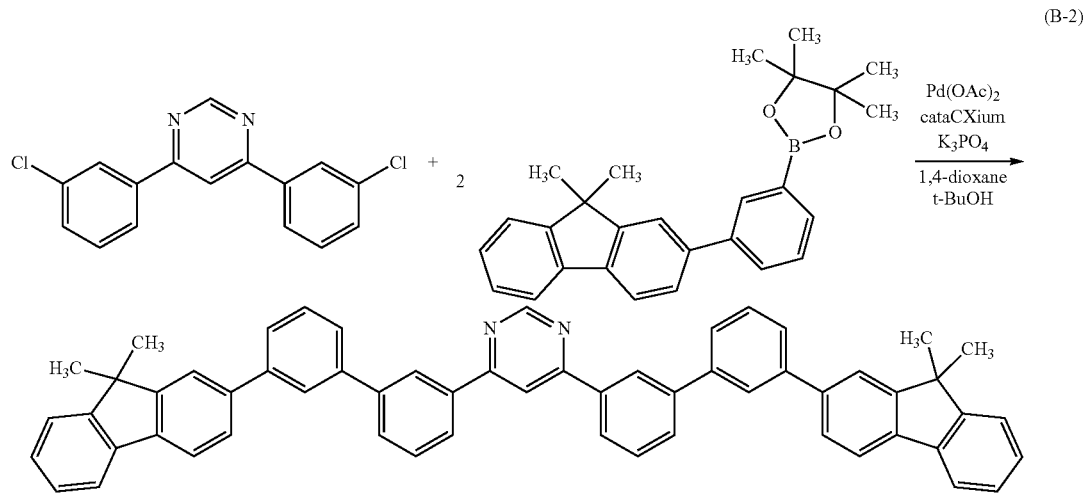

(B-2)

By a train sublimation method, 0.81 g of the obtained white solid was purified. In the purification by sublimation, the white solid was heated at 328° C. under a pressure of 2.7 Pa with a flow rate of argon gas of 10 mL/min. After the purification by sublimation, 0.52 g of a white solid which was a target substance was obtained at a collection rate of 64%.

The results of analysis by nuclear magnetic resonance ($^1$H-NMR chart) spectroscopy of the white solid obtained in Step 2 are described below. FIGS. 9A and 9B are $^1$H-NMR charts. FIG. 9B is a chart where the range from 7 ppm to 10 ppm on the horizontal axis (d) in FIG. 9A is enlarged. According to the result, 4,6mFBP2Pm (Structural Formula (109)), which is the heterocyclic compound of one embodiment of the present invention, was obtained in Step 2.

$^1$H NMR (CDCl$_3$, 500 MHz): δ (ppm)=1.54 (s, 12H), 7.31-7.37 (m, 4H), 7.46 (d, J=6.9 Hz, 2H), 7.57 (t, J=7.5 Hz, 2H), 7.63-7.70 (m, 10H), 7.75-7.95 (m, 6H), 7.93 (d, J=1.7 Hz, 2H), 8.16 (d, J=7.4 Hz, 2H), 8.24 (d, J=1.2 Hz, 1H), 8.45 (d, J=1.7 Hz, 2H), 9.38 (s, 1H).

Furthermore, 4,6mFBP2Pm was analyzed by LC/MS.

The analysis by LC/MS was carried out with Acquity UPLC (manufactured by Waters Corporation), and Xevo G2 Tof MS (manufactured by Waters Corporation).

In the MS, ionization was carried out by an electrospray ionization (abbreviation: ESI) method. At this time, the capillary voltage and the sample cone voltage were set to 3.0 kV and 30 V, respectively, and detection was performed in a positive mode. A component that underwent the ionization under the above-described conditions was collided with an argon gas in a collision cell to dissociate into product ions. The energy (collision energy) for the collision with argon was 70 eV. The mass range for the measurement was m/z=100 to 1200.

FIG. 10 shows the measurement result. According to the result in FIG. 10, product ions of 4,6mFBP2Pm, which is the heterocyclic compound of one embodiment of the present invention represented by Structural Formula (109), were detected mainly around m/z=769, m/z=754, m/z=738, and m/z=724. Note that the result in FIG. 10 shows characteristics derived from 4,6mFBP2Pm and therefore it can be said that the result is important data for identifying 4,6mFBP2Pm contained in the mixture.

Note that a peak around m/z=754 is presumed to be derived from cations in the state where a methyl group and a proton are dissociated from the compound represented by Structural Formula (109). A peak around m/z=738 is presumed to be derived from cations in the state where two methyl groups and a proton are dissociated. A peak around m/z=724 is presumed to be derived from cations in the state where three methyl groups and a proton are dissociated. This indicates that 4,6mFBP2Pm, which is the heterocyclic compound of one embodiment of the present invention, contains a plurality of methyl groups.

Example 3

In this example, Light-emitting element 1 was fabricated as a light-emitting element of one embodiment of the present invention. Light-emitting element 1 is described with reference to FIG. 11. Chemical formulae of materials used in this example are shown below.

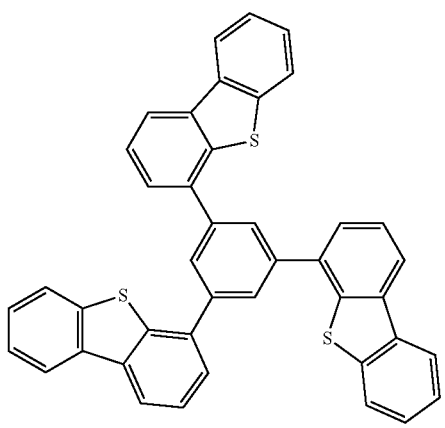

DBT3P-II

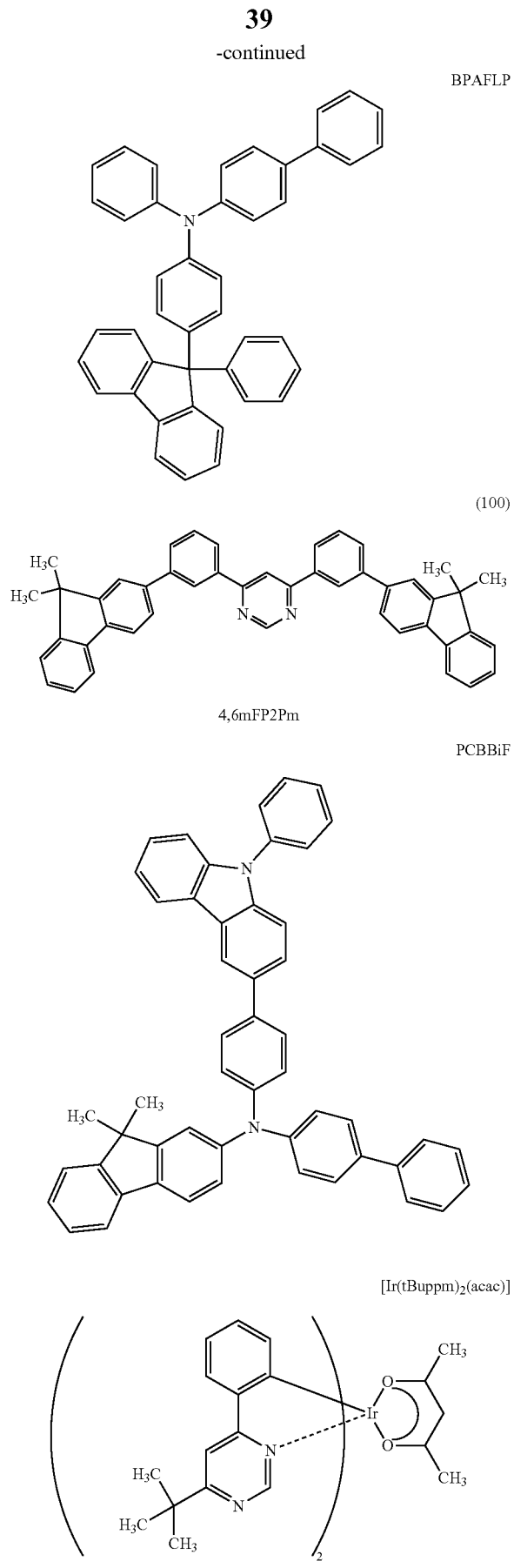

<<Fabrication of Light-Emitting Element 1>>

First, indium tin oxide containing silicon oxide (ITO-2) was deposited over a glass substrate 800 by a sputtering method, whereby a first electrode 801 functioning as an anode was formed. Note that the thickness was set to 110 nm and the electrode area was set to 2 mm×2 mm.

Next, as pretreatment for fabricating Light-emitting element 1 over the substrate 800, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and subjected to vacuum baking at 170° C. in a heating chamber of the vacuum evaporation apparatus for 30 minutes, and then the substrate 800 was cooled down for approximately 30 minutes.

Next, the substrate 800 was fixed to a holder provided in the vacuum evaporation apparatus so that a surface of the substrate over which the first electrode 801 was formed faced downward. In this example, a case is described in which a hole-injection layer 811, a hole-transport layer 812, a light-emitting layer 813, an electron-transport layer 814, and an electron-injection layer 815, which are included in an EL layer 802, are sequentially formed by a vacuum evaporation method.

After reducing the pressure in the vacuum evaporation apparatus to $10^{-4}$ Pa, 1,3,5-tri(dibenzothiophen-4-yl)benzene (abbreviation: DBT3P-II) and molybdenum(VI) oxide were deposited by co-evaporation so that the mass ratio of DBT3P-II to molybdenum oxide was 4:2, whereby the hole-injection layer 811 was formed over the first electrode 801. The thickness was 20 nm. Note that co-evaporation is an evaporation method in which a plurality of different substances are concurrently vaporized from different evaporation sources.

Next, 4-phenyl-4'-(9-phenylfluoren-9-yl)triphenylamine (abbreviation: BPAFLP) was deposited by evaporation to a thickness of 20 nm, whereby the hole-transport layer 812 was formed.

Next, the light-emitting layer 813 was formed over the hole-transport layer 812.

The light-emitting layer 813 having a stacked-layer structure was formed to a thickness of 40 nm as follows: 4,6mFP2Pm, N-(1,1'-biphenyl-4-yl)-N-[4-(9-phenyl-9H-carbazol-3-yl)phenyl]-9,9-dimethyl-9H-fluor en-2-amine (abbreviation: PCBBiF), and (acetylacetonato)bis(6-tert-butyl-4-phenylpyrimidinato)iridium(III) (abbreviation: [Ir(tBuppm)₂(acac)]) were deposited by co-evaporation to a thickness of 20 nm by co-evaporation so that the mass ratio of 4,6mFP2Pm to PCBBiF and [Ir(tBuppm)₂(acac)] was 0.7:0.3:0.05, and then 4,6mFP2Pm, PCBBiF, and [Ir(tBuppm)₂(acac)] were deposited by co-evaporation to a thickness of 20 nm so that the mass ratio of 4,6mFP2Pm to PCBBiF and [Ir(tBuppm)₂(acac)] was 0.8:0.2:0.05.

Next, the electron-transport layer 814 was formed over the light-emitting layer 813.

First, 4,6mFP2Pm was deposited by evaporation to a thickness of 25 nm and then bathophenanthroline (abbreviation: Bphen) was deposited by evaporation to a thickness of 10 nm, whereby the electron-transport layer 814 was formed.

Next, lithium fluoride was deposited by evaporation to a thickness of 1 nm over the electron-transport layer 814, whereby the electron-injection layer 815 was formed.

Finally, aluminum was deposited to a thickness of 200 nm over the electron-injection layer 815, whereby a second electrode 803 functioning as a cathode was formed. Through the above-described steps, Light-emitting element 1 was fabricated. Note that in all the above evaporation steps, evaporation was performed by a resistance-heating method.

Table 1 shows an element structure of Light-emitting element 1 fabricated as described above.

TABLE 1

|  | First electrode | Hole-injection layer | Hole-transport layer | Light-emitting layer | Electron-transport layer | | Electron-injection layer | Second electrode |
| --- | --- | --- | --- | --- | --- | --- | --- | --- |
| Light-emitting element 1 | ITO-2 (110 nm) | DBT3P-II:MoOx (4:2 20 nm) | BPAFLP (20 nm) | * | 4,6mFP2Pm (25 nm) | Bphen (10 nm) | LiF (1 nm) | Al (200 nm) |

* 4,6mFP2Pm:PCBBiF:[Ir(tBuppm)$_2$(acac)] (0.7:0.3:0.05 (20 nm)\0.8:0.2:0.05 (20 nm))

Light-emitting element 1 fabricated was sealed in a glove box under a nitrogen atmosphere so as not to be exposed to the air (specifically, a sealant was applied onto outer edges of the element, and at the time of sealing, first, UV treatment was performed and then heat treatment was performed at 80° C. for 1 hour).

<<Operation Characteristics of Light-Emitting Element 1>>

Operation characteristics of Light-emitting element 1 fabricated were measured. Note that the measurements were carried out at room temperature (in an atmosphere kept at 25° C.).

FIG. 12 shows current voltage-luminance characteristics of Light-emitting element 1. In FIG. 12, the vertical axis represents luminance (cd/m$^2$) and the horizontal axis represents voltage (V). FIG. 13 shows luminance-current efficiency characteristics of Light-emitting element 1. In FIG. 13, the vertical axis represents current efficiency (cd/A) and the horizontal axis represents luminance (cd/m$^2$). FIG. 14 shows voltage-current characteristics of Light-emitting element 1. In FIG. 14, the vertical axis represents current (mA) and the horizontal axis represents voltage (V).

FIG. 13 reveals that Light-emitting element 1 of one embodiment of the present invention has high efficiency. Table 2 shows initial values of main characteristics of Light-emitting element 1 at a luminance of approximately 1000 cd/m$^2$.

FIG. 15 shows an emission spectrum of Light-emitting element 1 to which current was applied at a current density of 25 mA/cm$^2$. As shown in FIG. 15, the emission spectrum of Light-emitting element 1 has a peak at around 545 nm. This indicates that green light derived from an organometallic complex [Ir(tBuppm)$_2$(acac)](abbreviation), which is a guest material used in the light-emitting layer, was obtained.

Next, Light-emitting element 1 was subjected to a reliability test. FIG. 16 shows the result of the reliability test. In FIG. 16, the vertical axis represents normalized luminance (%) with an initial luminance of 100%, and the horizontal axis represents driving time (h) of the element. Note that in the reliability test, Light-emitting element 1 was driven under the conditions where the initial luminance was 5000 cd/m$^2$ and the current density was constant. The results demonstrated that the luminance of Light-emitting element 1 after 100-hour driving was approximately 96% of the initial luminance.

Accordingly, Light-emitting element 1 in which the heterocyclic compound of one embodiment of the present invention (4,6mFP2Pm) was used in the light-emitting layer has high reliability. In addition, it was confirmed that the light-emitting element using the heterocyclic compound of one embodiment of the present invention has high efficiency and a long lifetime.

Example 4

In this example, Light-emitting elements 2 and 3 were fabricated as light-emitting elements of one embodiment of the present invention. Note that fabrication of Light-emitting elements 2 and 3 were the same as that of Light-emitting element 1 described in Example 3 except for some materials, ratio, thickness, and the like; thus, detailed description is omitted. Chemical formulae of materials used in this example are shown below.

TABLE 2

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
| --- | --- | --- | --- | --- | --- | --- | --- | --- |
| Light-emitting element 1 | 3.1 | 0.034 | 0.85 | (0.41, 0.58) | 830 | 98 | 99 | 26 |

DBT3P-II
BPAFLP
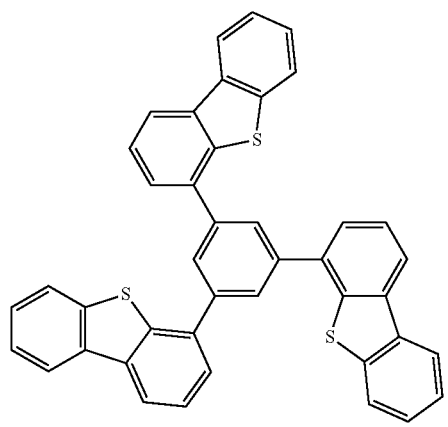
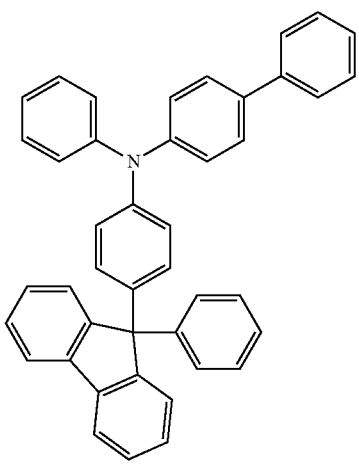
PCCP
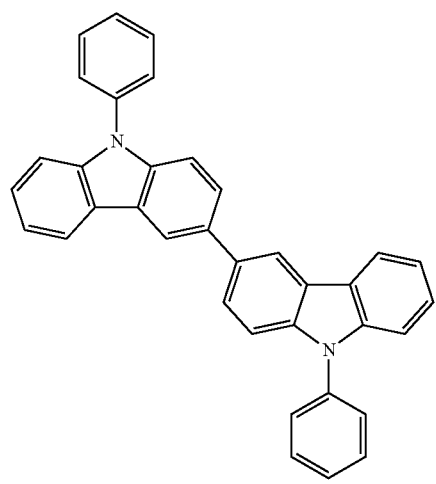
(109)
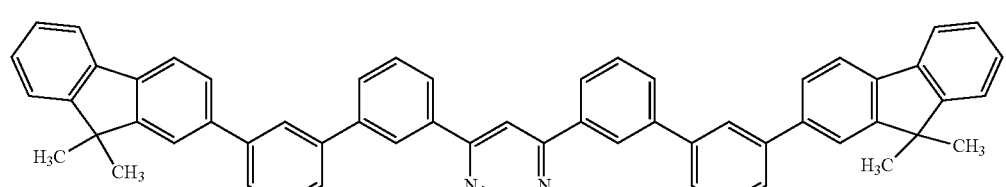
4,6mFBP2Pm
[Ir(ppy)₃]
[Ir(tBuppm)₂(acac)]
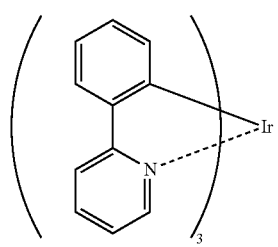
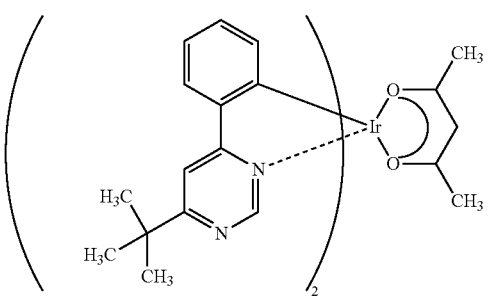

PCBBiF

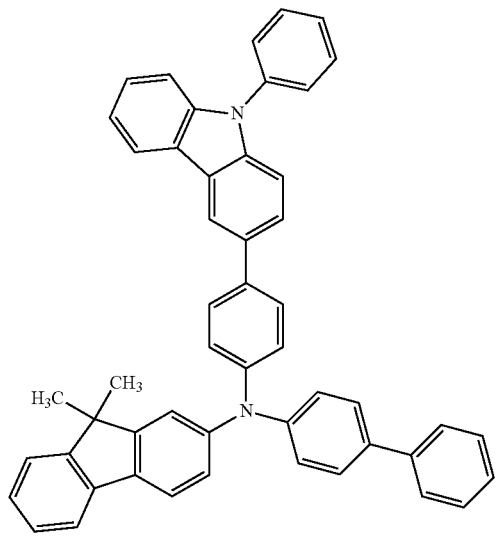

Bphen

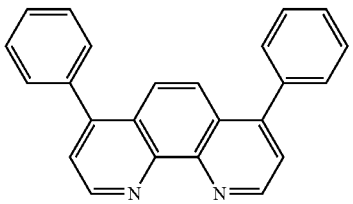

<<Fabrication of Light-Emitting Elements 2 and 3>>

Table 3 shows an element structure of each of Light-emitting elements 2 and 3 manufactured in this example. A first electrode of each of Light-emitting elements 2 and 3 was formed with indium tin oxide containing silicon oxide (ITO-3) by a sputtering method. A hole-transport layer of Light-emitting element 3 was formed with 9-phenyl-9H-3-(9-phenyl-9H-carbazol-3-yl)carbazole (abbreviation: PCCP). A light-emitting layer of each of Light-emitting elements 2 and 3 was formed with 4,6mFBP2Pm synthesized in Example 2.

TABLE 3

| | First electrode | Hole-injection layer | Hole-transport layer | Light-emitting layer | Electron-transport layer | Electron-injection layer | Second electrode |
|---|---|---|---|---|---|---|---|
| Light-emitting element 2 | ITO-3 (110 nm) | DBT3P-II:MoOx (4:2 60 nm) | BPAFLP (20 nm) | * | 4,6mFBP2Pm (20 nm) | Bphen (10 nm) | LiF (1 nm) | Al (200 nm) |
| Light-emitting element 3 | ITO-3 (110 nm) | DBT3P-II:MoOx (4:2 60 nm) | PCCP (20 nm) | ** | 4,6mFBP2Pm (20 nm) | Bphen (10 nm) | LiF (1 nm) | Al (200 nm) |

* 4,6mFBP2Pm:PCBBiF:[Ir(tBuppm)$_2$(acac)] (0.7:0.3:0.05 (20 nm)\0.8:0.2:0.05 (20 nm))
** 4,6mFBP2Pm:CCP:[Ir(ppy)$_3$](0.5:0.5:0.05 (20 nm)\0.8:0.2:0.05 (20 nm))

Each of Light-emitting elements 2 and 3 fabricated was sealed in a glove box under a nitrogen atmosphere so as not to be exposed to the air (specifically, a sealant was applied onto outer edges of the element, and at the time of sealing, first, UV treatment was performed and then heat treatment was performed at 80° C. for 1 hour).

<<Operation Characteristics of Light-Emitting Elements 2 and 3>>

Operation characteristics of Light-emitting elements 2 and 3 fabricated were measured. Note that the measurements were carried out at room temperature (in an atmosphere kept at 25° C.).

FIG. 17 and FIG. 21 show voltage-luminance characteristics of Light-emitting element 2 and Light-emitting element 3, respectively. In FIG. 17 and FIG. 21, the vertical axis represents luminance (cd/m$^2$) and the horizontal axis represents voltage (V). FIG. 18 and FIG. 22 show luminance-current efficiency characteristics of Light-emitting element 2 and Light-emitting element 3, respectively. In FIG. 18 and FIG. 22, the vertical axis represents current efficiency (cd/A) and the horizontal axis represents luminance (cd/m$^2$). FIG. 19 and FIG. 23 show voltage-current characteristics of Light-emitting element 2 and Light-emitting element 3, respectively. In FIG. 19 and FIG. 23, the vertical axis represents current (mA) and the horizontal axis represents voltage (V).

FIG. 18 and FIG. 22 reveal that Light-emitting elements 2 and 3 of one embodiment of the present invention have high efficiency. Table 4 shows initial values of main characteristics of Light-emitting elements 2 and 3 at a luminance of approximately 1000 cd/m$^2$.

TABLE 4

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 2 | 3.1 | 0.047 | 1.2 | (0.42, 0.57) | 1200 | 100 | 100 | 27 |
| Light-emitting element 3 | 3.6 | 0.053 | 1.3 | (0.32, 0.64) | 1100 | 84 | 73 | 23 |

The emission spectra of Light-emitting elements 2 and 3 to which current was applied at a current density of 25 mA/cm$^2$ were measured. FIG. 20 shows the emission spectrum of Light-emitting element 2, and FIG. 24 shows the emission spectrum of Light-emitting element 3. According to the results, the emission spectrum of Light-emitting element 2 has a peak at around 545 nm. This indicates that yellowish green light derived from an organometallic complex [Ir(tBuppm)$_2$(acac)]), which is a guest material used in the light-emitting layer, was obtained. In addition, the emission spectrum of Light-emitting element 3 has a peak at around 518 nm. This indicates that green light derived from an organometallic complex [Ir(ppy)$_3$], which is a guest material used in the light-emitting layer, was obtained.

Next, a reliability test of Light-emitting element 2 was performed. FIG. 25 shows the result of the reliability test. In FIG. 25, the vertical axis represents normalized luminance (%) with an initial luminance of 100% and the horizontal axis represents driving time (h) of the light-emitting element. Note that in the reliability test, Light-emitting element 2 was driven under the conditions where the initial luminance was set to 5000 cd/m$^2$ and the current density was constant. The result demonstrated that the luminance of Light-emitting element 2 after 100-hour driving was approximately 92% of the initial luminance.

Accordingly, the light-emitting element of one embodiment of the present invention has high reliability. In addition, it was confirmed that the light-emitting element using the heterocyclic compound of one embodiment of the present invention has high efficiency and a long lifetime.

This application is based on Japanese Patent Application serial no. 2014-106780 filed with Japan Patent Office on May 23, 2014, the entire contents of which are hereby incorporated by reference.

What is claimed is:

1. A light-emitting element comprising:
a pair of electrodes;
electroluminescent layer between the pair of electrodes;
a light-emitting layer in the electroluminescent layer;
a first layer on the light-emitting layer; and
a second layer on the first layer,
wherein the light-emitting layer comprises a phosphorescent substance, and
wherein the first layer comprises a compound represented by a formula (G1):

(G1)

wherein:
each of $A^1$ and $A^2$ independently represents one of nitrogen and carbon bonded to hydrogen;
at least one of $A^1$ and $A^2$ represents nitrogen;
Ar represents a substituted or unsubstituted arylene group having 6 to 18 carbon atoms;
B represents a substituted or unsubstituted 2-fluorenyl group; and
$R^1$ represents one of an alkyl group having 1 to 6 carbon atoms, and an aryl group having 6 to 13 carbon atoms.

2. A light-emitting device comprising the light-emitting element according to claim 1, comprising at least one of a transistor and a substrate.

3. An electronic device comprising the light-emitting device according to claim 2, comprising at least one of a microphone, a camera, an operation button, an external connection portion, and a speaker.

4. A lighting device comprising the light-emitting device according to claim 2, comprising at least one of a housing, a cover, and a support base.

5. The light-emitting element according to claim 1, wherein Bits the formula (G1) is represented by a formula (α):

(α)

wherein each of $R^{11}$ to $R^{19}$ independently represents one of hydrogen, an alkyl group having 1 to 6 carbon atoms, and an aryl group having 6 to 12 carbon atoms.

6. The light-emitting element according to claim 1, wherein B in the formula (G1) is represented by a formula (β):

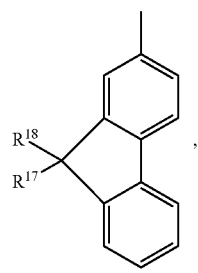 (β)
wherein each of $R^{17}$ and $R^{18}$ independently represents one of hydrogen, an alkyl group having 1 to 6 carbon atoms, and an aryl group having 6 to 12 carbon atoms.
7. The light-emitting element according to claim 1, wherein the second layer comprises a substance having an electron-transport property.
* * * * *